US012692272B2

(12) United States Patent
Flood et al.

(10) Patent No.: US 12,692,272 B2
(45) Date of Patent: Jul. 28, 2026

(54) SCALABLE ANION CAPTURE MACROCYCLES

(71) Applicants: INDIANA UNIVERSITY RESEARCH & TECHNOLOGY CORPORATION, Indianapolis, IN (US); Amar Hugh Flood, Bloomington, IN (US); James Robert Dobscha, Bloomington, IN (US)

(72) Inventors: Amar Hugh Flood, Bloomington, IN (US); James Robert Dobscha, Bloomington, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 565 days.

(21) Appl. No.: 18/104,469

(22) PCT Filed: Oct. 13, 2021

(86) PCT No.: PCT/US2021/054689
§ 371 (c)(1),
(2) Date: Feb. 1, 2023

(87) PCT Pub. No.: WO2022/081642
PCT Pub. Date: Apr. 21, 2022

(65) Prior Publication Data

US 2024/0262839 A1 Aug. 8, 2024

Related U.S. Application Data

(60) Provisional application No. 63/090,826, filed on Oct. 13, 2020.

(51) Int. Cl.
*C07D 487/22* (2006.01)
*C02F 1/68* (2023.01)
*C02F 101/12* (2006.01)

(52) U.S. Cl.
CPC ............ *C07D 487/22* (2013.01); *C02F 1/683* (2013.01); *C02F 2101/12* (2013.01)

(58) Field of Classification Search
None
See application file for complete search history.

(56) References Cited

U.S. PATENT DOCUMENTS 9,701,621 B2 7/2017 Flood et al.
10,077,233 B2 9/2018 Flood et al.
(Continued)

OTHER PUBLICATIONS

"Gauthier-Jaques et al.", "Synergy of Macrocycles and Macromolecular Topologies: An Efficient [34] Triazolophane-Based Synthesis of Cage-Shaped Polymers", ACS Macro Lett., 9, pp. 700-705, 2020. (Year: 2020).*
(Continued)

*Primary Examiner* — Jonathan M Peo
(74) *Attorney, Agent, or Firm* — Quarles & Brady LLP

(57) ABSTRACT

The present disclosure concerns scalable single-pot synthesis, anion binding features, liquid-liquid extraction of salts of the triazolophane macrocycle of Formula (I):
(Continued)

(I)

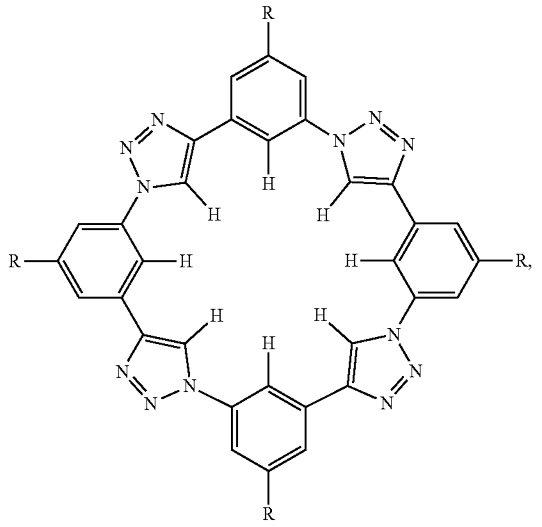

wherein the substituents R are independently selected from the group consisting of a linear and branched alkyl, a linear and branched alkyl substituted with an ionizable functional group such as an amine or carboxylic acid, a linear and branched alkoxy (R=—OR), an alkyl comprising $—O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

20 Claims, 5 Drawing Sheets

(56) References Cited

U.S. PATENT DOCUMENTS 10,202,395 B2 2/2019 Flood et al.
11,939,336 B2 * 3/2024 Flood .................... B01D 15/08

OTHER PUBLICATIONS

Li et al., "Strong, Size-Selective, and Electronically Tunable C—H—Halide Binding with Steric Control over Aggregation from Synthetically Modular, Shape-Persistent [34] Triazolophanes", J. Am. Chem. Soc., 130, 12111-12122, 2008. (Year: 2008).*
Stephenson, A.; Argent, S. P.; Riis-Johannessen, T.; Tidmarsh, I. S.; Ward, M. D., Structures and Dynamic Behavior of Large Polyhedral Coordination Cages: An Unusual Cage-to-Cage Interconversion. J. Am. Chem. Soc. 2011, 133, 858-870.
Thompson, M. C.; Busch, D. H., Reactions of Coordinated Ligands. IX. Utilization of the Template Hypothesis to Synthesize Macrocyclic Ligands in Situ. J. Am. Chem. Soc. 1964, 86, 3651-3656.
Vander Griend, D. A.; Bediako, D. K.; DeVries, M. J.; DeJong, N. A.; Heeringa, L. P., Detailed Spectroscopic, Thermodynamic, and Kinetic Characterization of Nickel(II) Complexes with 2,2'-Bipyridine and 1,10-Phenanthroline Attained via Equilibrium-Restricted Factor Analysis. Inorg. Chem. 2008, 47, 656-662.
Wagner, P.; Rominger, F.; Mastalerz, M., Switching the Statistical C3/C1 Ratio in the Threefold Aromatic Substitution of Tribenzotriquinacenes towards the C3 Isomer. Angew. Chem. Int. Ed. 2018, 57, 11321-11324.
Wang, Q.; Zhong, Y.; Miller, D. P.; Lu, X.; Tang, Q.; Lu, Z.-L.; Zurek, E.; Liu, R.; Gong, B., Self-Assembly and Molecular Recognition in Water: Tubular Stacking and Guest-Templated Discrete Assembly of Water-Soluble, Shape-Persistent Macrocycles. J. Am. Chem. Soc. 2020, 142, 2915-2924.
Yin, J.; Hu, Y.; Zhang, D.; Li, X.; Jin, W., Synthesis and characterization of symmetrical sulfur-fused polycyclic aromatic hydrocarbons with controlled shapes. Tetrahedron 2017, 73, 5794-5799.
Zhang, C.; Yu, C.; Long, H.; Denman, R. J.; Jin, Y.; Zhang, W., Synthesis of Phenylene Vinylene Macrocycles through Acyclic Diene Metathesis Macrocyclization and Their Aggregation Behavior. Chem. Eur. J. 2015, 21, 16935-16940.
Zhang, J.; Pesak, D. J.; Ludwick, J. L.; Moore, J. S., Geometrically-Controlled and Site-Specifically-Functionalized Phenylacetylene Macrocycles. J. Am. Chem. Soc. 1994, 116, 4227-4239.
Zhang, W.; Moore, J. S., Shape-Persistent Macrocycles: Structures and Synthetic Approaches from Arylene and Ethynylene Building Blocks. Angew. Chem. Int. Ed. 2006, 45, 4416-4439.
Zhao, D.; Moore, J. S., Shape-persistent arylene ethynylene macrocycles: syntheses and supramolecular chemistry. Chem. Commun. 2003, 807-818.
Zhou, X.-P.; Liu, J.; Zhan, S.-Z.; Yang, J.-R.; Li, D.; Ng, K.-M.; Sun, R. W.-Y.; Che, C.-M., A High-Symmetry Coordination Cage from 38- or 62-Component Self-Assembly. J. Am. Chem. Soc. 2012, 134, 8042-8045.
Duan Qunpeng et al., "Two new triazolophanes: synthesis, structures, self-assembling and anion complexation properties", Tetrahedron Letters, Elsevier, Amsterdam, NL, vol. 56, No. 26, Jun. 24, 2015, pp. 4002-4006.
European Patent Office, International Search Report and Written Opinion for corrsponding International Application No. PCT/US2021/054689, mailed Apr. 21, 2022.
Argent, S.P.; Jackson, F. C.; Chan, H. M.; Meyrick, S.; Taylor, C. G. P.; Ronson, T. K.; Rourke, J. P.; Ward, M. D., A family of diastereomeric dodecanuclear coordination cages based on inversion of chirality of individual triangular cyclic helicate faces. Chem. Sci. 2020, 11, 10167-10174.
Balakrishnan, K.; Datar, A.; Zhang, W.; Yang, X.; Naddo, T.; Huang, J.; Zuo, J.; Yen, M.; Moore, J. S.; Zang, L., Nanofibril Self-Assembly of an Arylene Ethynylene Macrocycle. J. Am. Chem. Soc. 2006, 128, 6576-6577.
Brooks, S. J.; García-Garrido, S. E.; Light, M. E.; Cole, P. A.; Gale, P. A., Conformational Control of Selectivity and Stability in Hybrid Amide/Urea Macrocycles. Chem. Eur. J. 2007, 13, 3320-3329.
Busch, D. H., First considerations: Principles, classification, and history of templates. Top. Curr. Chem. 2005, 249, 1-65.
Busch, D. H., The significance of complexes of macrocyclic ligands and their synthesis by ligand reactions. Record Chem. Progr. 1964, 25, 107-26.
Chang, K.-J.; Moon, D.; Lah, M. S.; Jeong, K.-S., Indole-Based Macrocycles as a Class of Receptors for Anions. Angew. Chem. Int. Ed. 2005, 44, 7926-7929.
Chen, L.; Chen, Q.; Wu, M.; Jiang, F.; Hong, M., Controllable Coordination-Driven Self-Assembly: From Discrete Metallocages to Infinite Cage-Based Frameworks. Acc. Chem. Res. 2015, 48, 201-210.
Choi, K.; Hamilton, A. D., A Dual Channel Fluorescence Chemosensor for Anions Involving Intermolecular Excited State Proton Transfer. Angew. Chem. Int. Ed. 2001, 40, 3912-3915.
Choi, K.; Hamilton, A. D., Rigid Macrocyclic Triamides as Anion Receptors: Anion-Dependent Binding Stoichiometries and 1H Chemical Shift Changes. J. Am. Chem. Soc. 2003, 125, 10241-10249.
Choi, K.; Hamilton, A. D., Selective Anion Binding by a Macrocycle with Convergent Hydrogen Bonding Functionality. J. Am. Chem. Soc. 2001, 123, 2456-2457.
Dalvie, D. K.; Kalgutkar, A. S.; Khojasteh-Bakht, S. C.; Obach, R. S.; O'Donnell, J. P., Biotransformation Reactions of Five-Membered Aromatic Heterocyclic Rings. Chem. Res. Toxicol. 2002, 15, 269-299.

(56) References Cited

OTHER PUBLICATIONS

Dobscha, J. R.; Castillo, H. D.; Li, Y.; Fadler, R. E.; Taylor, R. D.; Brown, A. A.; Trainor, C. Q.; Tait, S. L.; Flood, A. H., Sequence-Defined Macrocycles for Understanding and Controlling the Build-up of Hierarchical Order in Self-Assembled 2D Arrays. J. Am. Chem. Soc. 2019, 141, 17588-17600.
Du, Z.; Ren, C.; Ye, R.; Shen, J.; Maurizot, V.; Lu, Y.; Wang, J.; Zeng, H., BOPmediated one-pot synthesis of C5-symmetric macrocyclic pyridone pentamers. Chem. Commun. 2011, 47, 12488-12490.
Eller, L. R.; Stpień, M.; Fowler, C. J.; Lee, J. T.; Sessler, J. L.; Moyer, B. A., Octamethyl-octaundecylcyclo[8 pyrrole: A Promising Sulfate Anion Extractant. J. Am. Chem. Soc. 2007, 129, 11020-11021.
Feng, W.; Yamato, K.; Yang, L.; Ferguson, J. S.; Zhong, L.; Zou, S.; Yuan, L.; Zeng, X. C.; Gong, B., Efficient Kinetic Macrocyclization. J. Am. Chem. Soc. 2009, 131, 2629-2637.
Finke, A. D.; Gross, D. E.; Han, A.; Moore, J. S., Engineering Solid-State Morphologies in Carbazole-Ethynylene Macrocycles. J. Am. Chem. Soc. 2011, 133, 14063-14070.
Fu, H.; Chang, H.; Shen, J.; Yu, L.; Qin, B.; Zhang, K.; Zeng, H., An unusual macrocyclization reagent for highly selective one-pot synthesis of strained macrocyclic aromatic hexamers. Chem. Commun. 2014, 50, 3582-3584.
Gallant, A. J.; Hui, J. K. H.; Zahariev, F. E.; Wang, Y. A.; MacLachlan, M. J., Synthesis, Structure, and Computational Studies of Soluble Conjugated Multidentate Macrocycles. J. Org. Chem. 2005, 70, 7936-7946.
Gauthier-Jaques, M.; Theato, P., Synergy of Macrocycles and Macromolecular Topologies: An Efficient [34] Triazolophane-Based Synthesis of Cage-Shaped Polymers. ACS Macro Lett. 2020, 9, 700-705.
Gong, B., Hollow Crescents, Helices, and Macrocycles from Enforced Folding and Folding-Assisted Macrocyclization. Acc. Chem. Res. 2008, 41, 1376-1386.
Guieu, S.; Crane, A. K.; MacLachlan, M. J., Campestarenes: novel shape-persistent Schiff base macrocycles with 5-fold symmetry. Chem. Commun. 2011, 47, 1169-1171.
Haketa, Y.; Maeda, H., From Helix to Macrocycle: Anion-Driven Conformation Control of π-Conjugated Acyclic Oligopyrroles. Chem. Eur. J. 2011, 17, 1485-1492.
Jin, Y.; Zhang, A.; Huang, Y.; Zhang, W., Shape-persistent arylenevinylene macrocycles (AVMs) prepared via acyclic diene metathesis macrocyclization (ADMAC). Chem. Commun. 2010, 46, 8258-8260.
Kim, N.-K.; Chang, K.-J.; Moon, D.; Lah, M. S.; Jeong, K.-S., Two distinct anionbinding modes and their relative stabilities. Chem. Commun. 2007, 3401-3403.
Krygowski, T. M.; Szatylowicz, H.; Stasyuk, O. A.; Dominikowska, J.; Palusiak, M., Aromaticity from the Viewpoint of Molecular Geometry: Application to Planar Systems. Chem. Rev. 2014, 114, 6383-6422.
Lee, S.; Chen, C.-H.; Flood, A. H., A pentagonal cyanostar macrocycle with cyanostilbene CH donors binds anions and forms dialkylphosphate [3]rotaxanes. Nat. Chem. 2013, 5, 704-710.
Lee, S.; Hirsch, B. E.; Liu, Y.; Dobscha, J. R.; Burke, D. W.; Tait, S. L.; Flood, A. H., Multifunctional Tricarbazolo Triazolophane Macrocycles: One-Pot Preparation, Anion Binding, and Hierarchical Self-Organization of Multilayers. Chem. Eur. J. 2016, 22, 560-569.
Li, Y.; Flood, A. H., Pure C. H Hydrogen Bonding to Chloride lons: A Preorganized and Rigid Macrocyclic Receptor. Angew. Chem. Int. Ed. 2008, 47, 2649-2652.
Li, Y.; Flood, A. H., Strong, Size-Selective, and Electronically Tunable C—H •••Halide Binding with Steric Control over Aggregation from Synthetically Modular, Shape-Persistent [34]Triazolophanes. J. Am. Chem. Soc. 2008, 130, 12111-12122.
Li, Y.; Pink, M.; Karty, J. A.; Flood, A. H., Dipole-Promoted and Size-Dependent Cooperativity between Pyridyl- Containing Triazolophanes and Halides Leads to Persistent Sandwich Complexes with lodide. J. Am. Chem. Soc. 2008, 130, 17293-17295.
Liu, Y.; Shen, J.; Sun, C.; Ren, C.; Zeng, H., Intramolecularly Hydrogen-Bonded Aromatic Pentamers as Modularly Tunable Macrocyclic Receptors for Selective Recognition of Metal lons. J. Am. Chem. Soc. 2015, 137, 12055-12063.
Ma, C.; Lo, A.; Abdolmaleki, A.; MacLachlan, M. J., Synthesis and Metalation of Novel Fluorescent Conjugated Macrocycles. Org. Lett. 2004, 6, 3841-3844.
Meisel, J. W.; Hu, C. T.; Hamilton, A. D., Heterofunctionalized Cavitands by Macrocyclization of Sequence-Defined Foldamers. Org. Lett. 2019, 21, 7763-7767.
Mingos, D. M. P.; Rohl, A. L., Size and shape characteristics of inorganic molecules and ions and their relevance to molecular packing problems. Dalton Trans. 1991, 3419-3425.
Okochi, K. D.; Han, G. S.; Aldridge, I. M.; Liu, Y.; Zhang, W., Covalent Assembly of Heterosequenced Macrocycles and Molecular Cages through Orthogonal Dynamic Covalent Chemistry (ODCC). Org. Lett. 2013, 15, 4296-4299.
Okochi, K. D.; Jin, Y.; Zhang, W., Highly efficient one-pot synthesis of hetero-sequenced shape-persistent macrocycles through orthogonal dynamic covalent chemistry (ODCC). Chem. Commun. 2013, 49, 4418-4420.
Pruchyathamkorn, J.; Kendrick, W. J.; Frawley, A. T.; Mattioni, A.; Caycedo-Soler, F.; Huelga, S. F.; Plenio, M. B.; Anderson, H. L., A Complex Comprising a Cyanine Dye Rotaxane and a Porphyrin Nanoring as a Model Light-Harvesting System. Angew. Chem. Int. Ed. 2020, 59, 16455-16458.
Qiao, B.; Anderson, J. R.; Pink, M.; Flood, A. H., Size-matched recognition of large anions by cyanostar macrocycles is saved when solvent-bias is avoided. Chem. Commun. 2016, 52, 8683-8686.
Qin, B.; Jiang, L.; Shen, S.; Sun, C.; Yuan, W.; Li, S. F. Y.; Zeng, H., Folding-Promoted TBACI-Mediated Chemo- and Regioselective Demethylations of Methoxybenzene-Based Macrocyclic Pentamers. Org. Lett. 2011, 13, 6212-6215.
Qin, B.; Shen, S.; Sun, C.; Du, Z.; Zhang, K.; Zeng, H., One-Pot Multimolecular Macrocyclization for the Expedient Synthesis of Macrocyclic Aromatic Pentamers by a Chain Growth Mechanism. Chem. Asian J. 2011, 6, 3298-3305.
Ren, C.; Shen, J.; Zeng, H., One-Pot Synthesis of Strained Macrocyclic Pyridone Hexamers and Their High Selectivity toward Cu2+ Recognition. Org. Lett. 2015, 17, 5946-5949.
Ren, C.; Xu, S.; Xu, J.; Chen, H.; Zeng, H., Planar Macrocyclic Fluoropentamers as Supramolecular Organogelators. Org. Lett. 2011, 13, 3840-3843.
Rickhaus, M.; Jirasek, M.; Tejerina, L.; Gotfredsen, H.; Peeks, M. D.; Haver, R.; Jiang, H.-W.; Claridge, T. D. W.; Anderson, H. L., Global aromaticity at the nanoscale. Nat. Chem. 2020, 12, 236-241.
Rickhaus, M.; Vargas Jentzsch, A.; Tejerina, L.; Grubner, I.; Jirasek, M.; Claridge, T. D. W.; Anderson, H. L., Single- Acetylene Linked Porphyrin Nanorings. J. Am. Chem. Soc. 2017, 139, 16502-16505.
Roobottom, H. K.; Jenkins, H. D. B.; Passmore, J.; Glasser, L., Thermochemical Radii of Complex lons. J. Chem. Educ. 1999, 76, 1570.
Sanford, A. R.; Yamato, K.; Yang, X.; Yuan, L.; Han, Y.; Gong, B., Well-defined secondary structures. Euro. J. Biochem. 2004, 271, 1416-1425.
Seidel, D.; Lynch, V.; Sessler, J. L., Cyclo[8]pyrrole: A Simple-to-Make Expanded Porphyrin with No. Meso Bridges. Angew. Chem. Int. Ed. 2002, 41, 1422-1425.
Sheetz, E. G.; Qiao, B.; Pink, M.; Flood, A. H., Programmed Negative Allostery with Guest-Selected Rotamers Control Anion-Anion Complexes of Stackable Macrocycles. J. Am. Chem. Soc. 2018, 140, 7773-7777.
Shopsowitz, K. E.; Edwards, D.; Gallant, A. J.; MacLachlan, M. J., Highly substituted Schiff base macrocycles via hexasubstituted benzene: a convenient double Duff formylation of catechol derivatives. Tetrahedron 2009, 65, 8113-8119.

* cited by examiner $C_1$ $C_2$ $C_3$ $C_4$ $C_5$

| | $C_1$ | $C_2$ | $C_3$ | $C_4$ | $C_5$ |
|---|---|---|---|---|---|

| | | | | |
|---|---|---|---|---|
| 2019 | 2008 | 2016 | This Work | 2013 |
| Step Wise | Step Wise | One Pot | One Pot | One Pot |

SCALABLE ANION CAPTURE MACROCYCLES

CROSS-REFERENCE TO RELATED PATENT APPLICATIONS

This application is the U.S. national stage application of International Patent Application No. PCT/US2021/054689, filed Oct. 13, 2021, which claims benefit of priority under 35 U.S.C. 119 to U.S. Provisional Patent Application Ser. No. 63/090,826, filed Oct. 13, 2020, which is entitled "SCALABLE ANION CAPTURE MACROCYCLES," the contents of which are herein incorporated by reference in their entireties.

STATEMENT REGARDING FEDERALLY SPONSORED RESEARCH OR DEVELOPMENT

This invention was made with government support under SC0002728 awarded by Department Of Energy. The government has certain rights in the invention.

FIELD OF THE INVENTION

This invention pertains to the design and scalable synthesis of planar, anion-binding and shape-persistent macrocycles with $C_3$-$C_5$ symmetries by using one-pot macrocyclizations.

BACKGROUND OF THE INVENTION

Symmetry has touched every aspect of human society and has been married to scientific explorations since the days of ancient Greece when the elements were represented by Platonic solids composed of regular polygons (FIG. 1A). In the chemical sciences, symmetry is frequently used in synthesis, from building blocks like benzene and triazine, to molecular targets like hexabenzocoronene, and to supramolecular targets, such as cucurbiturils, and bigger to giant coordination cages and giant molecular wheels. Planar shape-persistent macrocycles are a class of molecule reminiscent of the regular polygons that have captured the imagination since antiquity. The geometric simplicity of these macrocycles also combines with a latent supramolecular functionality arising from the central cavity that can accommodate complementary guests. Their structure speaks to an underlying logic of synthesis that is expressed under ideal conditions as scalable one-pot reactions of simple difunctional monomers. These appealing geometric, synthetic and functional features mark these molecules as privileged. Many planar, shape-persistent macrocyclic systems have been made over the past two decades by Moore, Gong, Zeng, Hamilton, MacLachlan, ourselves and others. While many symmetries have been made, such as Hamilton's anion-binding $C_3$ macrocycles and Zeng's cation-binding $C_5$ pentamers, a complete series of functional macrocycles has yet to emerge.

Applicants have discovered a new shape-persistent macrocycle that completes a functional series of anion-binding, CH hydrogen bonding macrocycles (FIG. 1B) running from $C_1$ to $C_5$ covering the irregular and regular polygons alike.

BRIEF SUMMARY OF THE INVENTION

In a first aspect, a triazolophane macrocycle of Formula (I) is provided:

(I)

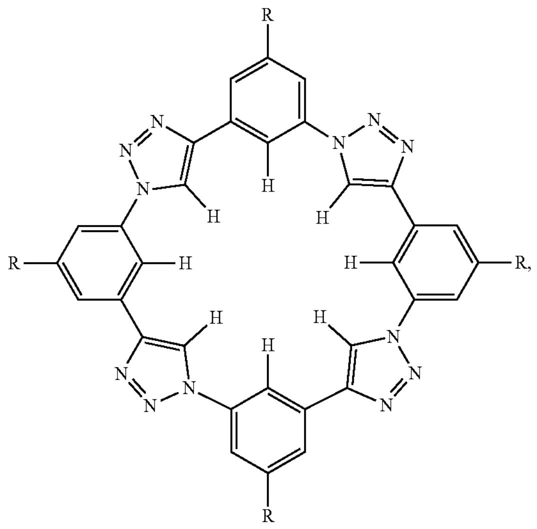

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

In a second aspect, a method of synthesizing a triazolophane macrocycle of Formula (I) is disclosed:

(I)

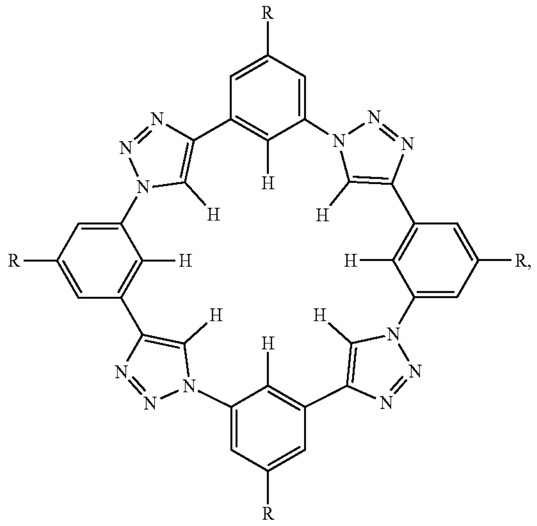

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising $—O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

The method includes a single-pot synthesis in the last step according to Scheme (I).

(Scheme (I)).

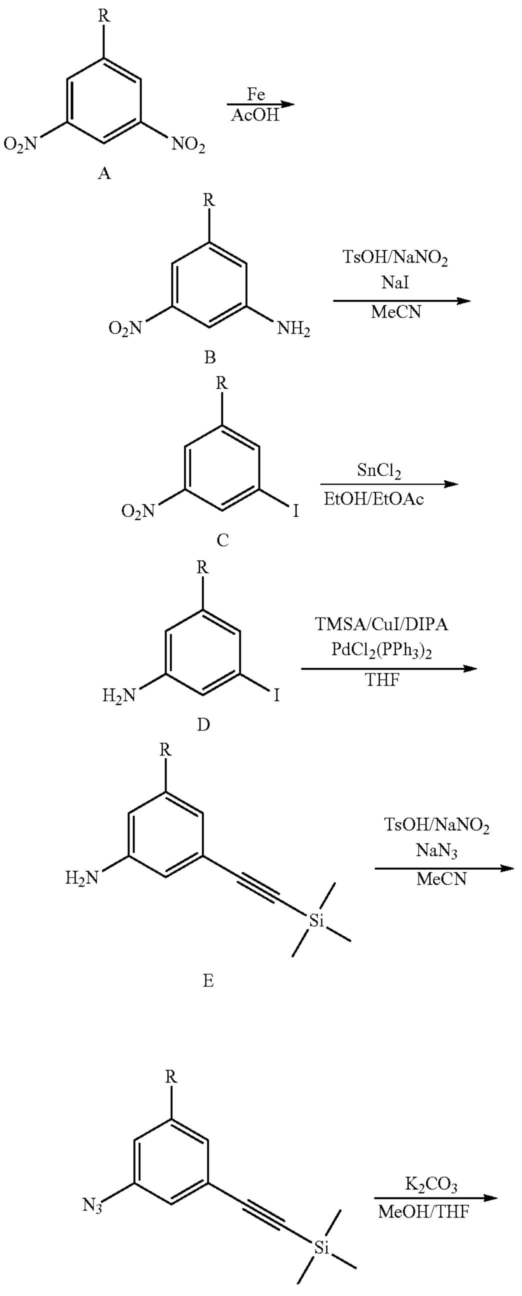

A B C D E F

-continued

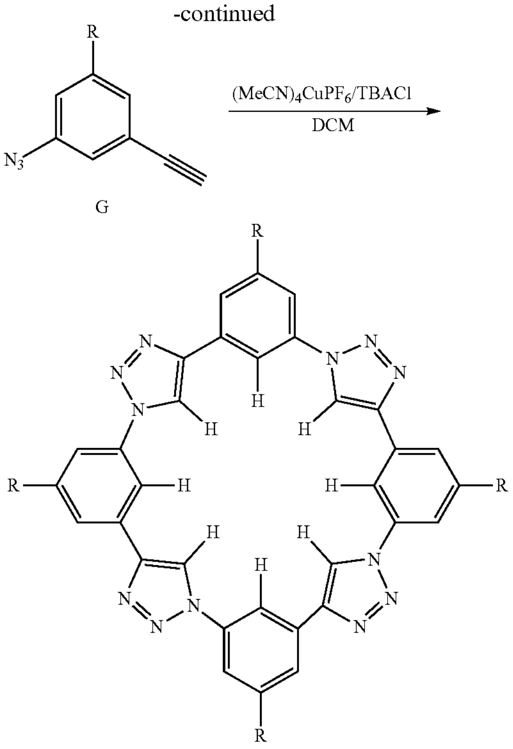

G (I)

In a third aspect, a method of increasing the yield and scale of the single-pot synthesis is provided that uses a halide salt as a template according to Scheme (X):

(Scheme (X)),

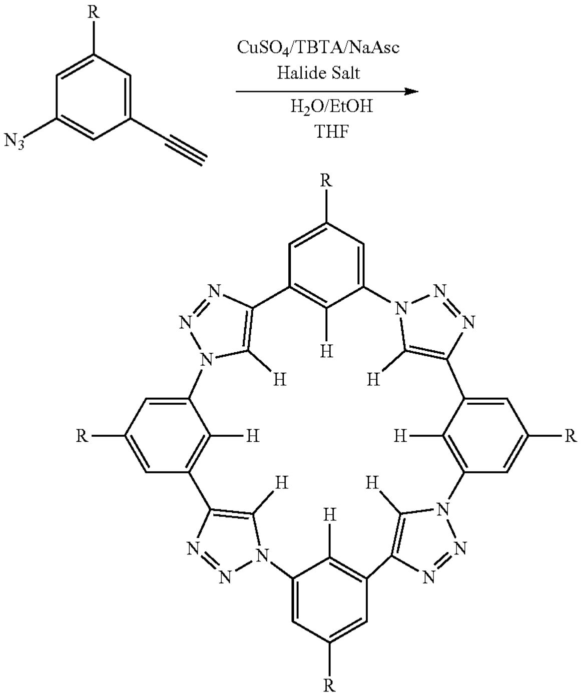

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

In a fourth aspect, a complex that includes (a) an anion and (b) a triazolophane macrocycle of Formula (I) is disclosed:

(I)

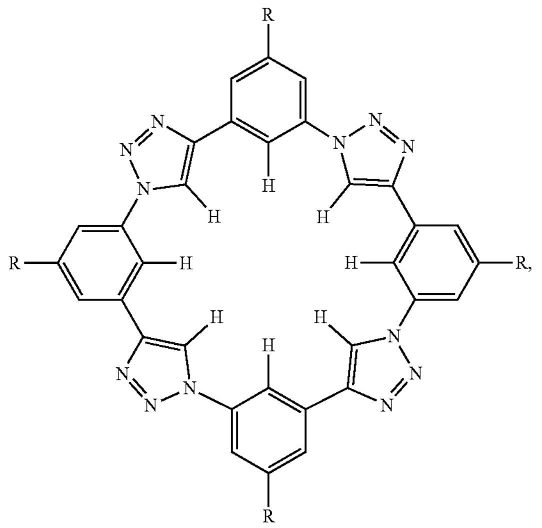

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

In a fifth aspect, a method of removing an anion from a solution containing the anion is disclosed. The method includes three steps. The first step includes contacting the solution with a triazolophane macrocycle of Formula (I):

(I)

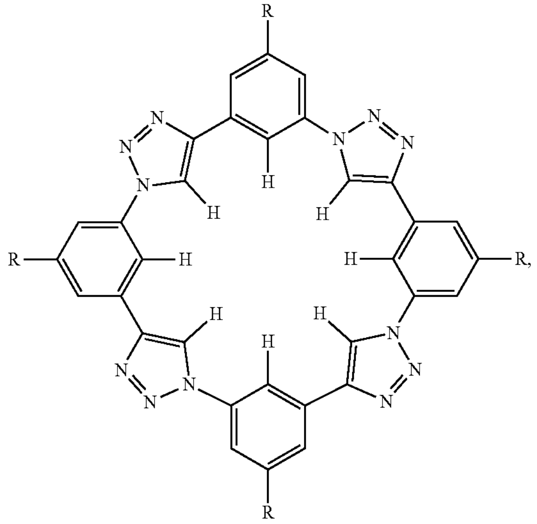

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

The second step includes forming a complex, said complex comprising the anion and the triazolophane macrocycle of Formula (I). The third step includes removing the complex from the solution.

In a sixth aspect, a composition comprising a triazolophane macrocycle of Formula (I) is provided:

(I)

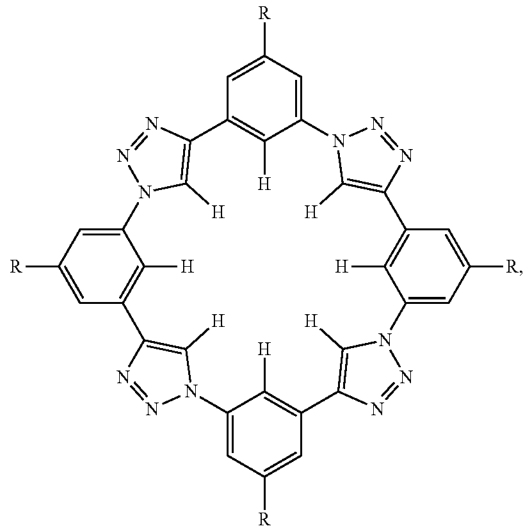

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising $—O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

DETAILED DESCRIPTION

Figure 1A:
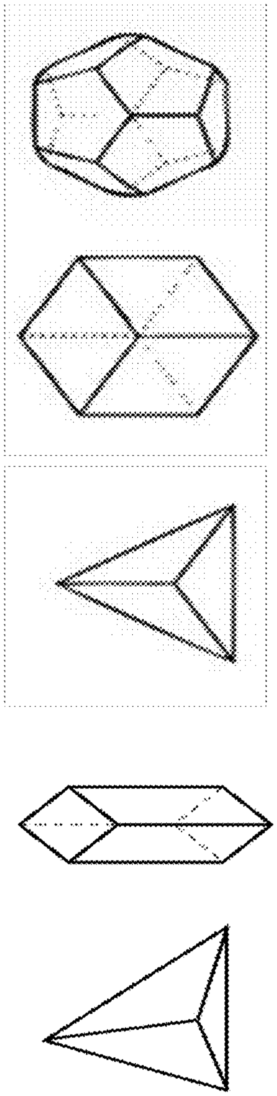
FIG. 1A depicts irregular and platonic solids described by early Greek philosophers composed of various polygons.
Figure 1B:
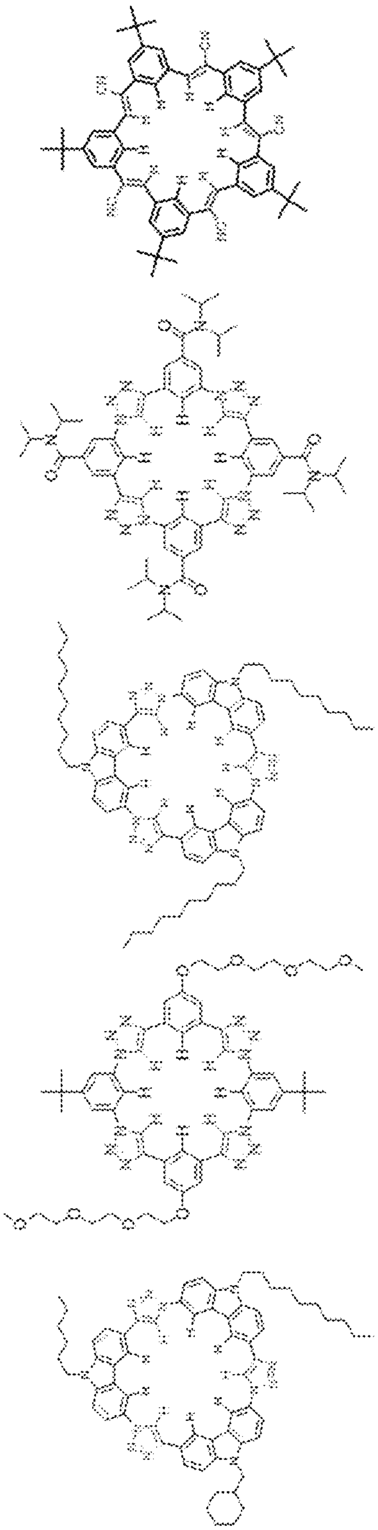
FIG. 1B depicts an exemplary series of planar, shape-persistent, CH hydrogen bonding and anion-binding macrocyclic frameworks of increasing symmetry from the prior art (compound structures $C_1$, $C_2$, $C_3$ and $C_5$) and the newly-designed anion-binding macrocycle having $C_4$-symmetry of the present disclosure (compound structure C4).

The present disclosure is based on the discovery of a scalable, single-pot synthesis of a novel triazolophane macrocycle of Formula (I):

(I)

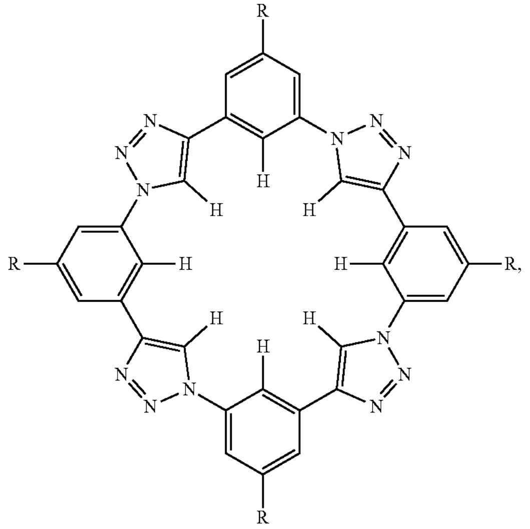

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising $—O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

The triazolophane macrocycle compound of Formula (I) displays high affinity for anions and can act as anion receptors or chelators. The compound displays robust affinity for chloride. The selectivity for chloride is also high relative to other anions tested (fluoride and iodide). The compounds can be used in methods to remove chloride salts from water by extracting the chloride salt into a suitable organic solvent (dichloromethane).

Definitions

When introducing elements of aspects of the disclosure or particular embodiments, the articles "a," "an," "the," and "said" are intended to mean that there are one or more of the elements. The terms "comprising," "including," and "having" are intended to be inclusive and mean that there may be additional elements other than the listed elements. The term "or" means any one member of a particular list and also includes any combination of members of that list, unless otherwise specified.

As intended herein, the terms "substantially," "approximately," and "about" and similar terms are intended to have a broad meaning in harmony with the common and accepted usage in the art to which the subject matter of this disclosure pertains. It should be understood by those of skill in the art who review this disclosure that these terms are intended to allow a description of certain features described and claimed without restricting the scope of these features to precise numerical ranges provided. Accordingly, these terms should be interpreted as indicating that insubstantial or inconsequential modifications or alterations of the subject matter described and claimed are considered to be within the scope of the invention as recited in the appended claims.

The compound herein described may exhibit chirality and may be isolated in either optically active or racemic forms. Methods for preparing optically active forms include, for instance, resolution of racemic forms or synthesis from optically active starting materials. Many geometric isomers of olefins, C═N double bonds, and the like can also be present in the compounds described herein, and all such stable isomers are contemplated in the present invention. All chiral, diastereomeric, racemic forms and all geometric isomeric forms of a structure are intended, unless the specific stereochemistry or isomeric form is specifically indicated.

The compound herein described may exist as salts. The term "salt," refers to salts or zwitterions of the compounds which are water or oil-soluble or dispersible. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the present compound by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent, provided that the resulting bond is present in a stable compound.

The term "hydroxy" as used herein, refers to an —OH group. The term "oxo" as used herein, refers to a =O group. The term "oxy" as used herein, refers to a —O— group. The term "sulfonyl" as used herein, refers to a $—S(O)_2—$ group. The term "carbonyl" as used herein refers to a —C(O)— group. The term "carboxy" as used herein refers to a —C(O)—OH group. The term "halo" or "halogen," as used herein, refers to —Cl, —Br, —I or —F.

The term "alkenyl" as used herein, refers to a straight or branched chain hydrocarbon group containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, hexyloxy, heptyloxy, octyloxy, nonyloxy, decyloxy, undecyloxy, dodecyloxy, trisdecyloxy, tetradecyloxy, and pentadecyloxy.

The term "alkyl" as used herein, refers to a straight or branched chain hydrocarbon group containing from 1 to 15 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkyl-NH" as used herein, refers to an alkyl group, as defined herein, appended to the parent molecular moiety through a nitrogen atom.

The term "alkyl-NH-alkyl" as used herein, refers to an alkyl-NH group, as defined herein, appended to the parent molecular moiety through an alkyl group, as defined herein.

The term "aryl" as used herein, means a phenyl group, or a bicyclic or a tricyclic fused ring system. Bicyclic fused ring systems are exemplified by a phenyl group appended to the parent molecular moiety and fused to a monocyclic cycloalkyl group, as defined herein, a phenyl group, a monocyclic heteroaryl group, as defined herein, or a monocyclic heterocycle, as defined herein. Tricyclic fused ring systems are exemplified by an aryl bicyclic fused ring system, as defined herein and fused to a monocyclic cycloalkyl group, as defined herein, a phenyl group, a monocyclic heteroaryl group, as defined herein, or a monocyclic heterocycle, as defined herein. Representative examples of aryl include, but are not limited to, anthracenyl, azulenyl, fluorenyl, indanyl, indenyl, naphthyl, phenyl and tetrahydronaphthyl.

The term "cycloalkyl" as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic fused ring systems are exemplified by a cycloalkyl group appended to the parent molecular moiety, which is fused to an additional cycloalkyl group, as defined herein, a phenyl group, a heteroaryl, as defined herein, or a heterocycle as defined herein. Tricyclic fused ring systems are exemplified by a cycloalkyl bicyclic fused ring system fused to an additional cycloalkyl group, as defined herein, a phenyl group, a heteroaryl, as defined herein, or a heterocycle as defined herein. Bicyclic ring systems are also exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane and bicyclo[4.2.1]nonane. Tricyclic ring systems are also exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.03,7]nonane and tricyclo[3.3.1.13,7]decane (adamantane).

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "heteroaryl," as used herein, refers to an aromatic monocyclic ring or an aromatic bicyclic ring system. The aromatic monocyclic rings are five or six membered rings containing at least one heteroatom independently selected from the group consisting of N, O and S. The five membered aromatic monocyclic rings have two double bonds and the six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, benzimidazolyl, benzofuranyl, benzothiazolyl, benzothienyl, benzoxazolyl, furyl, imidazolyl, indazolyl, indolyl, indolizinyl, isobenzofuranyl, isoindolyl, isoxazolyl, isoquinolinyl, isothiazolyl, naphthyridinyl, oxadiazolyl, oxazolyl, phthalazinyl, pyridinyl, pyridazinyl, pyridyl, pyrimidinyl, pyrazinyl, pyrazolyl, pyrrolyl, quinolinyl, quinolizinyl, quinoxalinyl, quinazolinyl, tetrazolyl, thiadiazolyl, thiazolyl, thienyl, triazolyl and triazinyl.

The term "heterocycle" as used herein, refers to a non-aromatic monocyclic ring or a non-aromatic bicyclic ring. The non-aromatic monocyclic ring is a three, four, five, six, seven, or eight membered ring containing at least one heteroatom, independently selected from the group consisting of N, O and S. Representative examples of monocyclic ring systems include, but are not limited to, azetidinyl, aziridinyl, diazepinyl, dithianyl, imidazolinyl, imidazolidinyl, isothiazolinyl, isoxazolinyl, isoxazolidinyl, morpholinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydro-2H-pyranyl, tetrahydro-2H-pyran-2-yl, tetrahydro-2H-pyran-4-yl, tetrahydrothienyl, thiazolinyl, thiazolidinyl, thiomorpholinyl, 1,1-dioxidothiomorpholinyl (thiomorpholine sulfone) and thiopyranyl. The bicyclic heterocycles are exemplified by a monocyclic heterocycle appended to the parent molecular moiety and fused to a monocyclic cycloalkyl group, as defined herein, a monocyclic aryl group, a monocyclic heteroaryl group, as defined herein, or a monocyclic heterocycle, as defined herein. Bicyclic ring systems are also exemplified by a bridged monocyclic ring system in which two non-adjacent atoms of the monocyclic ring are linked by a bridge of between one and three atoms selected from the group consisting of carbon, nitrogen and oxygen. Representative examples of bicyclic ring systems include but are not limited to, for example, benzopyranyl, benzothiopyranyl, benzodioxinyl, 1,3-benzodioxolyl, cinnolinyl, 1,5-diazocanyl, 3,9-diaza-bicyclo[4.2.1]non-9-yl, 3,7-diazabicyclo[3.3.1]nonane, octahydro-pyrrolo[3,4-c]pyrrole, indolinyl, isoindolinyl, 2,3,4,5-tetrahydro-1H-benzo[c]azepine, 2,3,4,5-tetrahydro-1H-benzo[b]azepine, 2,3,4,5-tetrahydro-1H-benzo[d]azepine, tetrahydroisoquinolinyl and tetrahydroquinolinyl.

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that a compound name is misnamed or otherwise conflicts with the chemical structure disclosed herein.

C4-Symmetric Triazolophane Macrocycle Compound

In a first aspect, a triazolophane macrocycle of Formula (I) is provided:

(I)

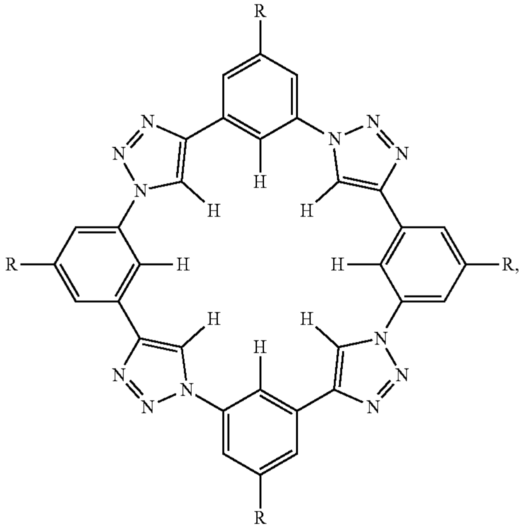

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

In a first respect, the substituents R of the triazolophane macrocycle of Formula (I) are identical. In a second respect, the triazolophane macrocycle of Formula (I) is the triazolophane macrocycle of Formula (IA):

(IA)

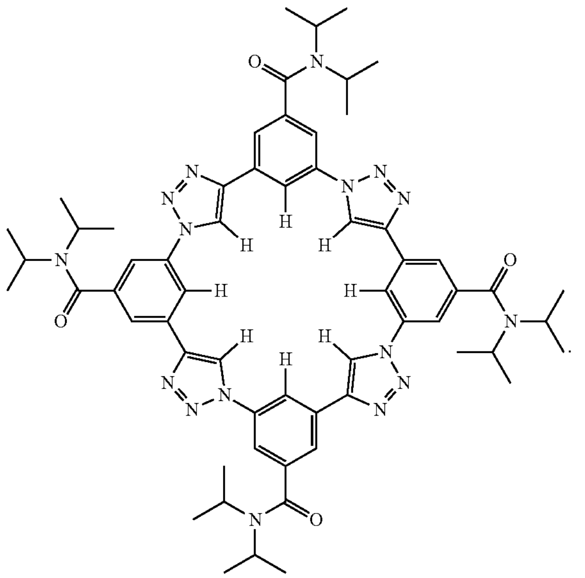

Scalable, Single-Pot Synthetic Method for Producing the Compound of Formula (I)

In a second aspect, a method of synthesizing a triazolophane macrocycle of Formula (I) is provided:

(I)

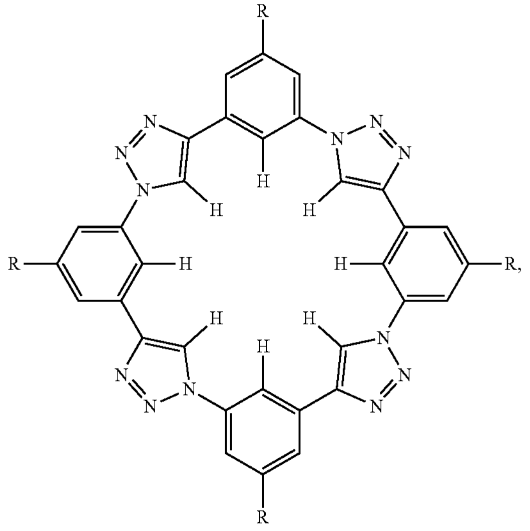

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent, wherein the method comprises a single-pot synthesis according to Scheme (I):

(Scheme (I)).

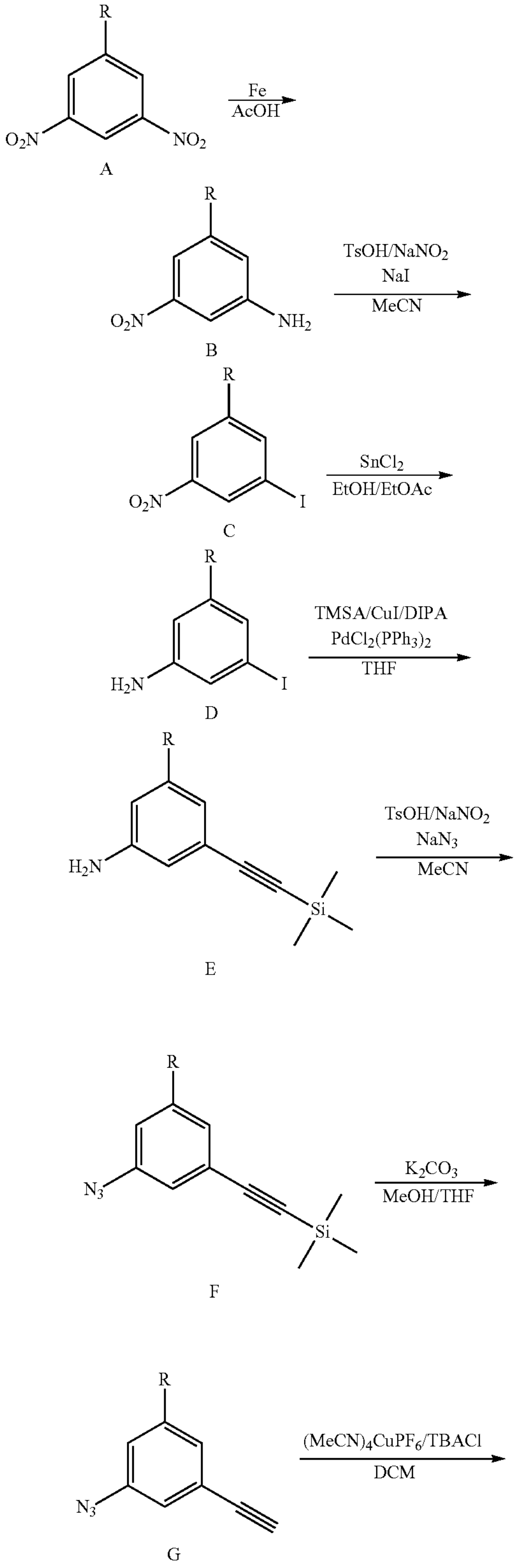

-continued

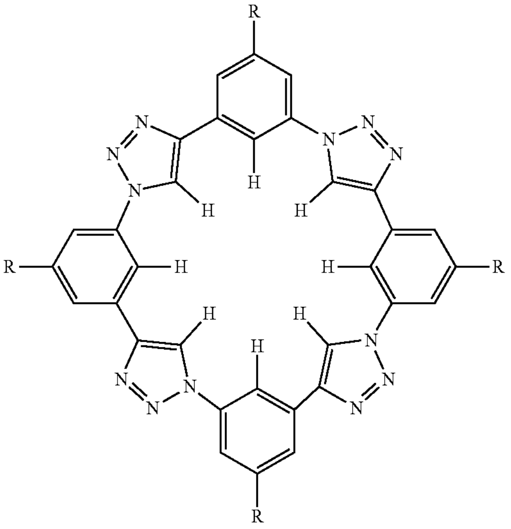

(I)

In a first respect, the method of synthesizing the triazolophane macrocycle of Formula (I) is provided, wherein the substituents R of the triazolophane macrocycle of Formula (I) are identical. In a second aspect, the method of synthesizing a triazolophane macrocycle of Formula (I) is dis closed, wherein the triazolophane macrocycle of Formula (I) is Formula (IA):

(IA)

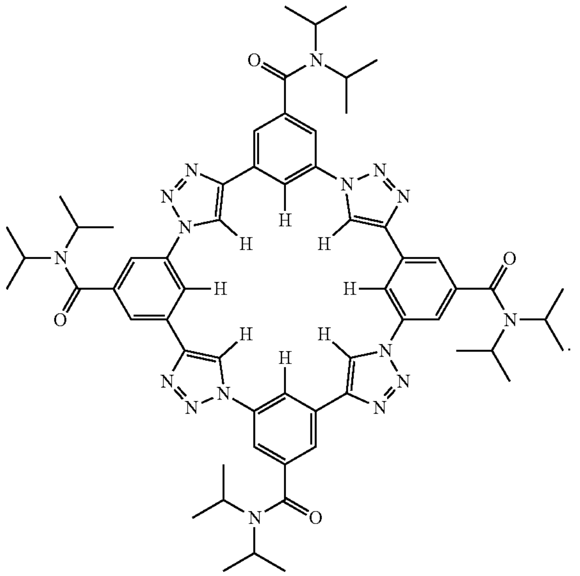

The method includes a single-pot synthesis according to Scheme (IA):

(Schene (IA).

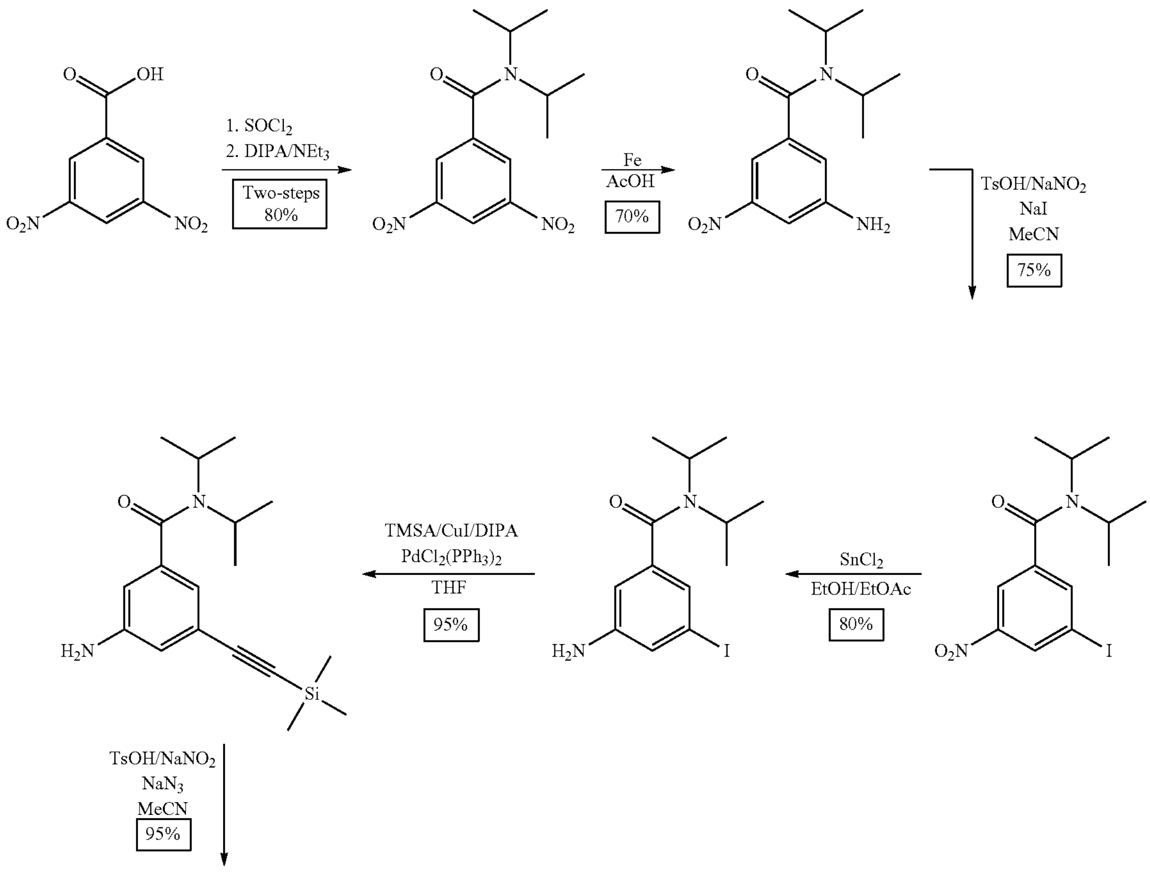

-continued

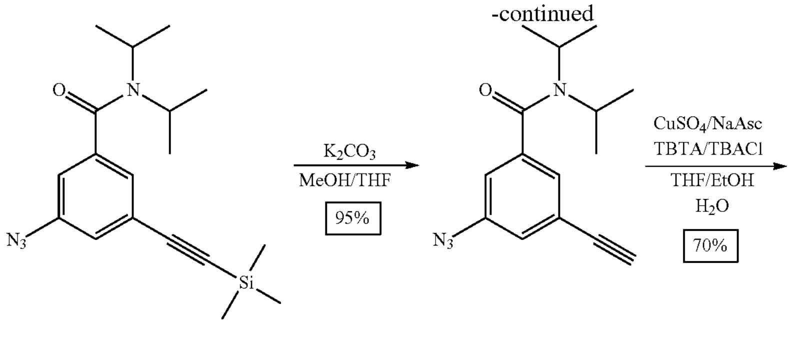

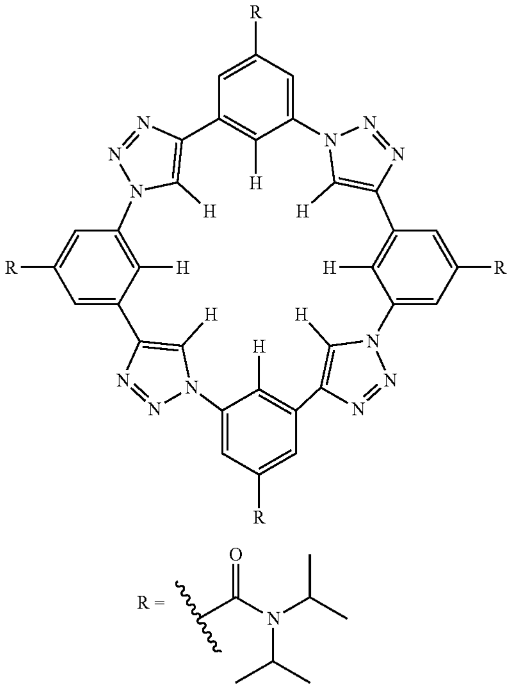

The synthesis of the $C_4$-symmetric triazolophane macrocycles was inspired by the one-pot syntheses of the $C_3$ triazolophanes that utilized a single difunctional carbazole as a building block. The one-pot triazolophane, OPTz, was synthesized in eight steps (Scheme (IA)) from commercial starting material 3,5-dinitrobenzoic acid. After amidation, symmetry was broken by selective reduction of one nitro group. After functional group transformation, difunctional building block 8 was afforded as the key precursor in 30% over seven steps.

The resulting product of the synthesis reaction can be purified using methods well understood and conventional in the art. A preferred purification method includes column chromatography. Improvements in yield and scale can be obtained by inclusion of a suitable salt as a templating guest anion, such as a chloride-based salt.

Anionic Guest Templating Effects on $C_4$-Symmetric Triazolophane Macrocycles

Applicants discovered that the addition of a catalytic amount of certain anions (e.g., chloride, fluoride, or iodide) to the one-pot CuAAC reaction of amide 8 can resulted in dramatic improvements in yield of the OPTZ macrocycle (25%-70% overall yield). This intermediate yield suggests that the templating anionic guest is deactivated by binding to the OPTZ macrocycle as it is produced over the course of the reaction. Furthermore, this is consistent with the characteristically strong binding affinity of triazolophane macrocycles for the guest anion.

Accordingly, in a third aspect, a method of increasing the yield and scale of the single-pot synthesis is provided that uses a halide salt as a template according to Scheme (X):

(Scheme (X)),

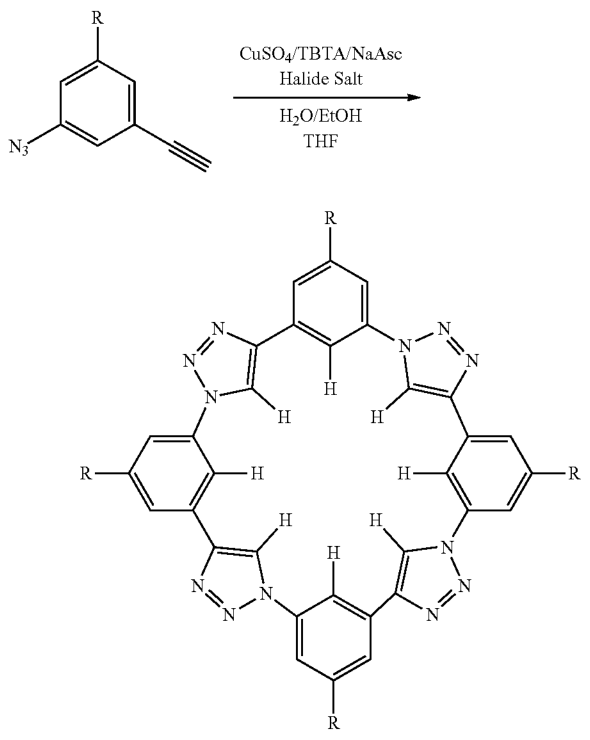

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

In a first respect, the halide salt of Scheme (X) comprises an anion selected from the group consisting of chloride, fluoride and iodide. In a second respect the halide salt of Scheme (X) is a chloride salt. In a third respect, as shown below in Scheme (Y), the synthesis of the triazolophane macrocycle of Formula (I) is the triazolophane macrocycle of Formula (IA) (the OPTz macrocycle):

(Scheme (Y)).

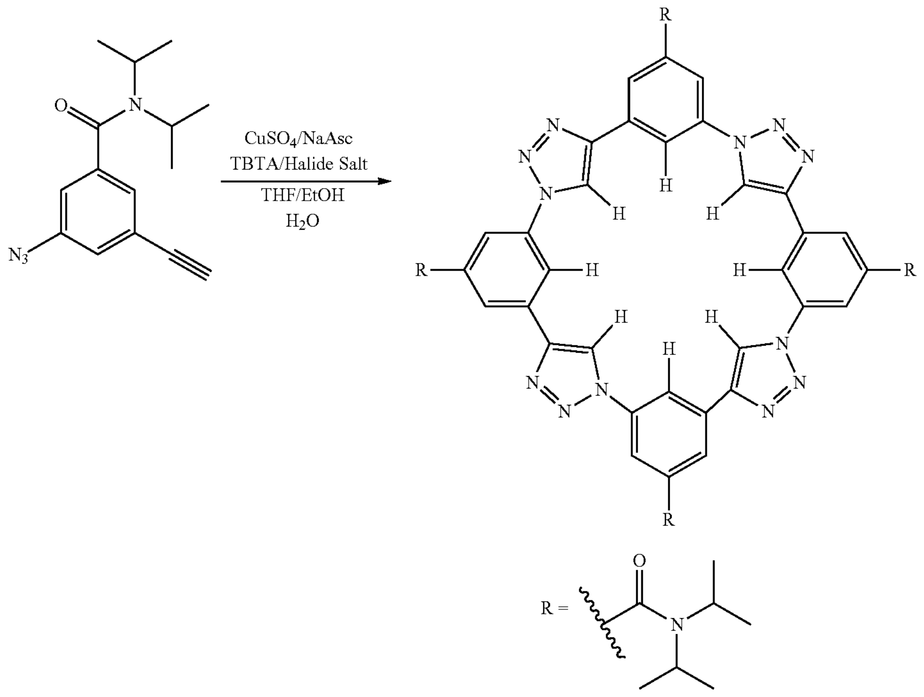

In a fourth respect, the halide salt of Scheme (Y) comprises an anion selected from the group consisting of chloride, fluoride and iodide. In a fifth respect, the halide salt of Scheme (Y) is a chloride salt, such as tetrabutylammonium chloride.

Complexes

The triazolophane macrocycle of Formula (I) displays surprisingly robust affinity and selectivity for anions present in salt solutions. Exemplary anions having the ability to complex with the triazolophane macrocycle of Formula (I) include, but are not limited to, chloride, fluoride, iodide, bromide, hydroxide, sulfide, hydrogen sulfide, cyanide, azide, organosulfides (R—S$^-$, where R=anything organic), alkoxides (R—O$^-$, where R=anything organic), bifluoride, borohydride, tetrafluoroborate, hydride, bisulfide, selenide, hydrogen selenide, superoxide, peroxide, and hypochlorite.

Accordingly, in a fourth aspect, a complex that includes (a) an anion and (b) a triazolophane macrocycle of Formula (I) is disclosed:

(I)

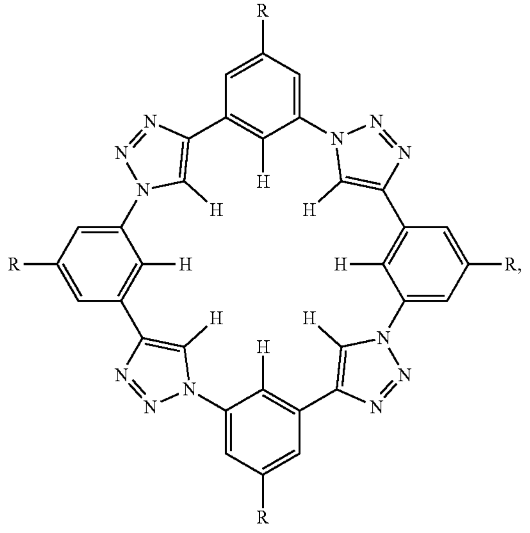

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —O($CH_2CH_2O$)$_n$$CH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

In a first respect, the triazolophane macrocycle of Formula (I) has identical substituents R. In a second respect, the triazolophane macrocycle of Formula (I) is the triazolophane macrocycle of Formula (IA):

(IA)

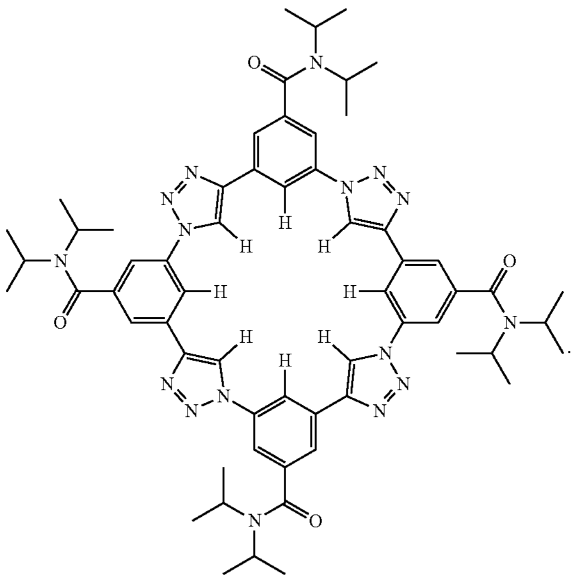

In a third respect, the anion may be selected from the group consisting of but not limited to chloride, fluoride, iodide, bromide, hydroxide, sulfide, hydrogen sulfide, cyanide, azide, organosulfides (R—S$^-$, where R=any organic group), alkoxides (R—O$^-$, where R=any organic group), bifluoride, borohydride, tetrafluoroborate, hydride, bisulfide, selenide, hydrogen selenide, superoxide, peroxide, and hypochlorite. In a fourth respect, a ratio of the complex comprising the triazolophane macrocycle of Formula (I): anion is selected from but not limited to 1:1 (macrocycle: anion), 2:1 (macrocycle:anion), and 3:2 (macrocycle:anion).

Methods Using an Aryl-Triazole Bicyclic Macrocycle to Remove an Anion from a Solution The ability to form high affinity complexes with anions makes it possible to use triazolophane macrocycle of Formula (I) in a method to facilitate extracting chloride salts without the presence of a complementary cation-binding site. Accordingly, in a fifth aspect, a method of removing an anion from a solution containing the anion is disclosed. The method includes several steps. The first step includes contacting the solution with a triazolophane macrocycle of Formula (I):

(I)

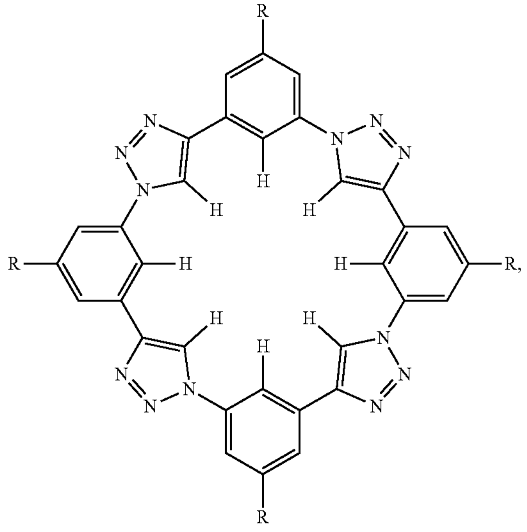

wherein the substituent R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

The second step includes forming a complex, said complex comprising the anion and the triazolophane macrocycle of Formula (I). The third step includes removing the complex from the solution. In a first respect, exemplary anions include those selected from the group consisting of chloride, fluoride and iodide.

In a first respect, the triazolophane macrocycle of Formula (I) has identical substituents R. In a second respect, the triazolophane macrocycle of Formula (I) is the triazolophane macrocycle of Formula (IA):

(IA)

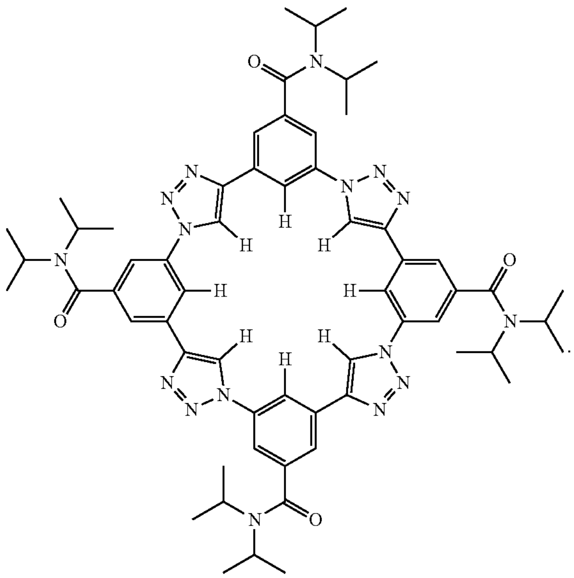

Compositions

In a sixth aspect, a composition comprising a triazolophane macrocycle of Formula (I) is provided:

(I)

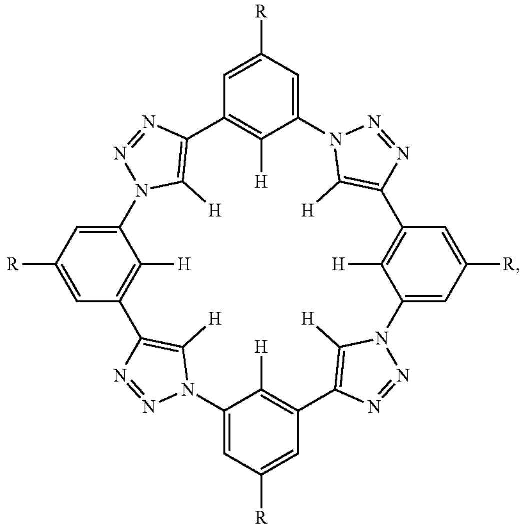

wherein the substituents R are independently selected from the group consisting of a linear and branched alkyl, a linear and branched alkyl substituted with an ionizable functional group such as an amine or carboxylic acid, a linear and branched alkoxy (R=—OR), an alkyl comprising —$O(CH_2CH_2O)_nCH_3$, where n is 1-20, an amide —CO—$NR^1R^2$, where $R^1$ is any alkyl, organic substituent, $R^2$ is any alkyl, organic substituent, wherein $R^1$ and $R^2$ may be identical or different, —OCO—R, wherein R is any alkyl, organic substituent, an aromatic ring and their substituted analogues, any length and sequence of natural and unnatural amino acids that make up a peptide chain, and —C≡C—R where R is any alkyl, organic substituent.

In a first respect, the triazolophane macrocycle of Formula (I) of the composition has identical substituents R. In a second respect, the triazolophane macrocycle of Formula (I) is the triazolophane macrocycle of Formula (IA):

(IA)

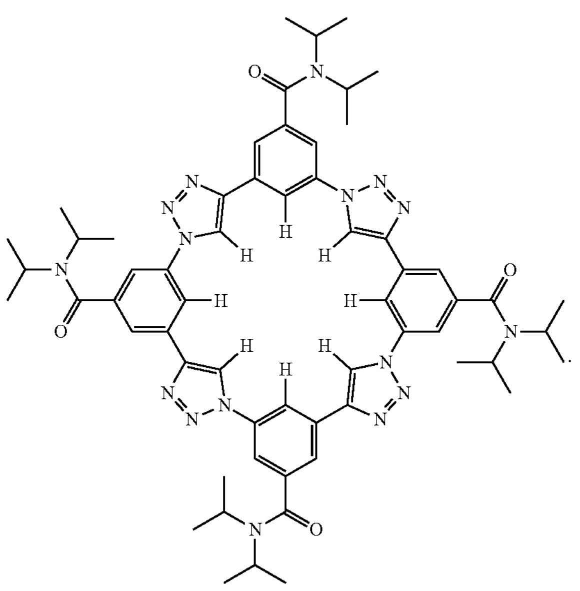

EXAMPLES

Example 1. General Synthetic Procedures

Reagents were obtained from commercial suppliers and used as received unless otherwise noted. Column chromatography was performed on silica gel (160-200 mesh, Sorbent Technologies, USA). Thin-layer chromatography (TLC) was performed on pre-coated silica gel plates (0.25 mm thick, #1615126, Sorbent Technologies, USA) and observed under UV light. Nuclear magnetic resonance (NMR) spectra were recorded on Varian Inova (600 MHz, 500 MHz, and 400 MHz) and Varian VXR (400 MHz) spectrometers at room temperature (298 K) unless otherwise indicated. Chemical shifts were referenced to residual solvent peaks. High-resolution electrospray ionization and electron ionization mass spectrometry (HR-ESI-MS and HR-EI-MS) was performed on a Thermo Electron Corporation MAT 95XP-Trap mass spectrometer.

Example 2. Synthesis of the Triazolophane Macrocycle of Formula (IA)

Synthesis of the triazolophane macrocycle of Formula (IA) was carried out using Scheme (I).

Scheme 1. Synthesis of triazolophane macrocycle of Formula (IA) (OPTz).

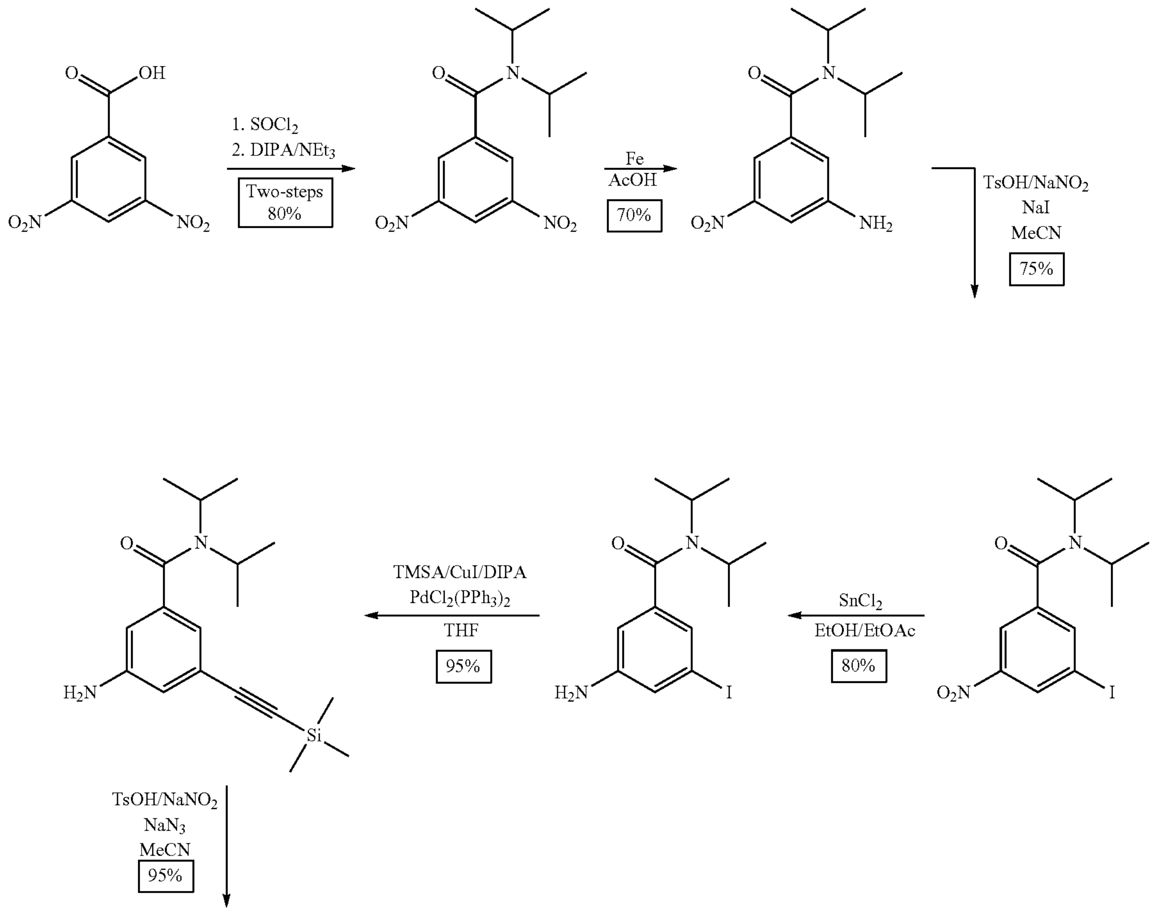

-continued

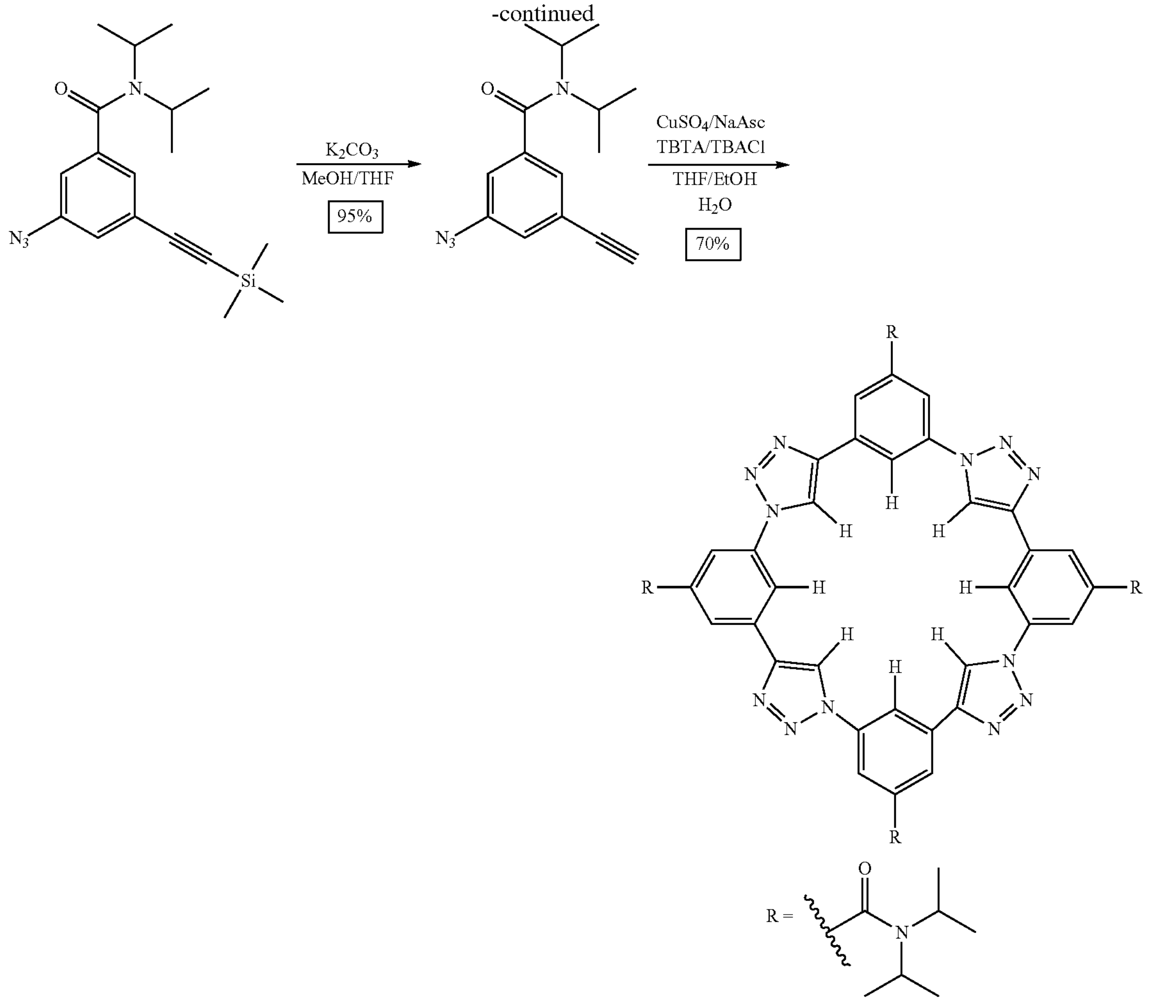

The synthesis of the $C_4$-symmetric triazolophane macrocycle was inspired by the one-pot syntheses of the $C_3$ triazolophanes that utilized a single difunctional carbazole as a building block. One-pot triazolophane, OPTz, was synthesized in eight steps (Scheme (I)) from commercial starting material 3,5-dinitrobenzoic acid. After amidation, symmetry was broken by selective reduction of one nitro group. After functional group transformation, difunctional building block 8 was afforded as the key precursor in 30% over seven steps.

The $C_4$-symmetric triazolophane macrocycle, OPTz, was characterized using standard methods, as described in Example 3.

Prior to carrying out a one-pot CuAAC with building block 8, the viability of the one-pot macrocyclization was examined by using computation. A conformational analysis of the pre-macrocyclic oligomer (MM2, Supporting Information) returned 105 low-energy conformations. The conformer that is preorganized to form the OPTz macrocycle sits 31 kJ $mol^{-1}$ higher in energy than the lowest energy conformer. The low statistical population of the macrocycle-forming conformer prompted us to consider employing a templating guest to collapse the number of conformations sampled by the pre-macrocyclic oligomer. Satisfyingly, subjecting building block 8 to one-pot copper catalyzed azide-alkyne cycloaddition (CuAAC) conditions with 1 equivalent of tetrabutylammonium chloride (TBACl), relative to the product macrocycle, triazolophane OPTz was obtained with a 70% isolated yield. This success motivated us to explore a more exhaustive range of reaction conditions to understand and optimize the role of templation on the one-pot synthesis.

Example 3. Detailed Synthesis and Characterization of Novel Compounds

N,N-diisopropyl-3,5-dinitrobenzamide (1)

(1)

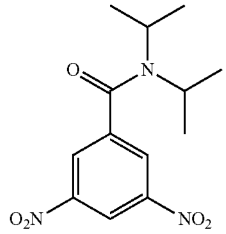

3,5-dinitrobenzoic acid (50 g, 236 mmol) was refluxed for 2 hours in a solution of chloroform (85 mL) and thionyl chloride (86 mL, 1.2 mol). The solution was then cooled and concentrated under reduced pressure to give the acid chloride as a tan solid that was used immediately without further purification. The tan solid was then dissolved in dry dichloromethane (200 mL) and cooled to 0° C. A mixture of triethylamine (165 mL, 1.2 mol) and diisopropylamine (50 mL, 354 mmol) were then slowly added to the dichloromethane solution. The solution then stirred for 12 hours while warming to room temperature. The dichloromethane solution was then washed with three portions (150 mL) of a saturated aqueous solution of potassium bicarbonate. The organic portion was then dried over $MgSO_4$, filtered, and concentrated to give the crude product as a brown solid. Column chromatography on silica gel with 3:1 hexanes: ethyl acetate as eluent gave pure compound 1 as a light brown solid (55.5 g, 188 mmol, 80% over two steps). The $^1H$ NMR spectrum was identical to previous reports.

3-amino-N,N-diisopropyl-5-nitrobenzamide (2)

(2)

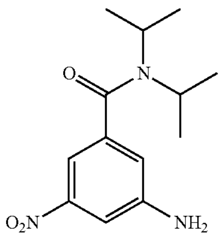

Compound 1 (55.5 g, 188 mmol) was dissolved in glacial acetic acid (300 mL) and heated to 120° C. Iron filings (31.5 g, 564 mmol) were added in three portions over a period of 30 minutes and the mixture was refluxed and the progress of the reaction was tracked by TLC (3:1 dichloromethane:ethyl acetate), typically the reaction was complete within 3 hours of the last addition of iron filings. The hot reaction mixture was then poured over ice, filtered, and then extracted with 3 portions of 200 mL of dichloromethane. The combined organic fractions were then washed with 6 portions of 150 mL of brine, dried over $MgSO_4$, filtered, and dried to give crude compound 2 as a tan solid. Column chromatography on silica gel with 3:1 dichloromethane:ethyl acetate as eluent gave pure compound 2 as a tan solid (35 g, 132 mmol, 70% yield). $^1H$ NMR (400 MHz, Chloroform-d) δ/ppm=7.48-7.42 (m, 2H), 6.87 (t, J=1.8 Hz, 1H), 3.64 (d, J=92.2 Hz, 2H), 1.33 (d, J=132.1 Hz, 12H). $^{13}C$ NMR (126 MHz, Chloroform-d) δ/ppm=168.57, 149.14, 147.91, 140.98, 117.44, 110.02, 109.06, 30.91, 20.65. HRMS (CI) calculated for $C_{13}H_{19}N_3O_3$+H: 266.1499 $[M+H]^+$; found: 266.1500.

3-iodo-N,N-diisopropyl-5-nitrobenzamide (3)

(3)

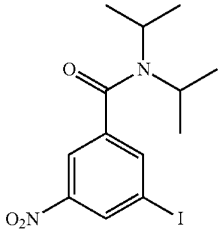

Compound 2 (35 g, 132 mmol) and p-toluenesulfonic acid monohydrate (75 g, 396 mmol) were dissolved in acetonitrile (250 ml) and cooled to 0° C. (ice bath) resulting in a brown slurry. A solution of $NaNO_2$ (18.2 g, 264 mmol) in water (15 mL) was added dropwise, and the mixture was stirred for 1 hour. A solution of NaI (49.5 g, 330 mmol) in water (15 mL) was then added drop-wise, followed by stirring for 1 hour at 0° C. The mixture was warmed to room temperature and stirred for an additional 30 min. The organic phase was dried over $MgSO_4$ and concentrated in vacuo to give crude compound 3 as a light brown solid. Column chromatography on silica gel with 5:1 dichloromethane: ethyl acetate as eluent gave pure compound 3 as a tan solid (37.2 g, 99 mmol, 75% yield). $^1H$ NMR (400 MHz, Chloroform-d) δ/ppm=8.54 (d, J=1.9 Hz, 1H), 8.10 (s, 1H), 7.94 (s, 1H), 3.62 (s, 2H), 1.52 (d, J=112.9 Hz, 12H). $^{13}C$ NMR (126 MHz, Chloroform-d) δ/ppm=166.47, 148.30, 141.46, 140.46, 132.41, 120.04, 93.82, 29.71, 20.64. HRMS (ESI) calculated for $C_{13}H_{17}N_2O_3I$+H: 377.0357 $[M+H]^+$; found: 377.0358.

3-amino-5-iodo-N,N-diisopropylbenzamide (4)

(4)

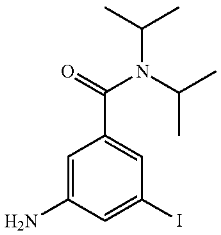

Compound 3 (37.2 g, 99 mmol) and $SnCl_2 \cdot 2\ H_2O$ (112 g, 495 mmol) in EtOAc (150 mL) and EtOH (150 mL) was heated at reflux for 8 hours. After cooling to room temperature, the reaction mixture was poured into a saturated aqueous solution of $Na_2CO_3$ and adjusted to a pH of 9, then stirred for 2 hours. The resulting slurry was then filtered, and extracted with dichloromethane. The organic phases were combined, dried over $MgSO_4$, filtered, and concentrated in vacuo to give crude amino benzamide 5 as a light brown solid. Column chromatography on silica gel with 4:1 dichloromethane:ethyl acetate as eluent gave pure compound 4 as a light brown solid (27.5 g, 79.2 mmol, 80% yield). $^1H$ NMR (500 MHz, Chloroform-d) δ/ppm=7.01 (t, J=1.9 Hz, 1H), 6.96 (t, J=1.4 Hz, 1H), 6.53 (dd, J=2.2, 1.3 Hz, 1H), 3.49 (d, J=175.2 Hz, 2H), 1.30 (d, J=176.3 Hz, 12H). $^{13}C$ NMR (126 MHz, Chloroform-d) δ/ppm=169.27, 148.00, 141.45, 123.83, 123.69, 111.31, 94.84, 20.65. HRMS (ESI) calculated for $C_{13}H_{19}IN_2O$+H: 347.0616 $[M+H]^+$; found: 347.0615.

3-amino-N,N-diisopropyl-5-((trimethylsilyl)ethynyl) benzamide (5)

(5)

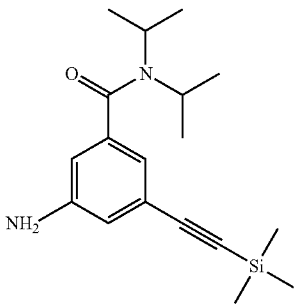

To a degassed solution of compound 4 (27.5 g, 79.2 mmol) and diisopropylamine (55 mL, 396 mmol) in THE (200 mL) was added [$PdCl_2(PPh_3)_2$] (1.1 g, 1.6 mmol), CuI (762 mg, 4 mmol), and trimethylsilylacetylene (17 mL, 119 mmol). The reaction mixture was stirred under an argon atmosphere for 1 hour and quenched with a 1 M aqueous solution of ammonium chloride (75 mL). The mixture was extracted with dichloromethane, the organic phase was dried over $MgSO_4$, filtered, and concentrated in vacuo to give compound 5 as a brown solid (23.8 g, 75.3 mmol, 95% yield). $^1$H NMR (400 MHz, Chloroform-d) δ/ppm=6.85 (s, 1H), 6.81 (s, 1H), 6.64 (s, 1H), 3.64 (d, J=136.8 Hz, 2H), 1.21 (d, J=136.8 Hz, 12H), 0.20 (s, 9H). HRMS (APCI) calculated for $C_{18}H_{25}N_2OSi$+H: 317.2044 $[M+H]^+$; found: 317.2049.

3-azido-N,N-diisopropyl-5-((trimethylsilyl)ethynyl) benzamide (6)

(6)

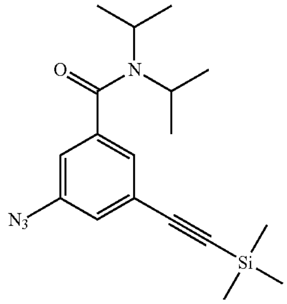

Compound 5 (23.8 g, 75.3 mmol) and p-toluenesulfonic acid monohydrate (43 g, 226 mmol) were dissolved in acetonitrile (200 ml) and cooled to 0° C. (ice bath) resulting in a brown slurry. A solution of $NaNO_2$ (5.7 g, 83 mmol) in water (10 mL) was added dropwise, and the mixture was stirred for 1 hour. A solution of $NaN_3$ (5.9 g, 90.4 mmol) in water (10 mL) was then added drop-wise, followed by stirring for 1 hour at 0° C. The mixture was warmed to room temperature and stirred for an additional 30 min. The solution was then basified to a pH of 9 with a 1 M aqueous solution of NaOH. The solution was then extracted with dichloromethane, the organic phase was dried over $MgSO_4$ and then concentrated in vacuo to give compound 6 as a dark brown solid (24.5 g, 71.5 mmol, 95% yield). $^1$H NMR (400 MHz, Chloroform-d) δ/ppm=7.12 (t, J=1.4 Hz, 1H), 7.07 (dd, J=2.2, 1.3 Hz, 1H), 6.85 (dd, J=2.2, 1.4 Hz, 1H), 3.60 (d, J=78.4 Hz, 2H), 1.34 (d, J=134.0 Hz, 12H), 0.22 (s, 9H). HRMS (APCI) calculated for $C_{18}H_{26}N_4OSi$+H: 343.1949 $[M+H]^+$; found: 343.1952.

3-azido-5-ethynyl-N,N-diisopropylbenzamide (7)

(7)

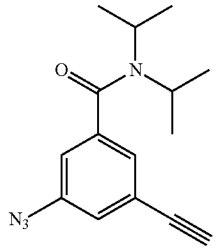

Compound 6 (24.5 g, 71.5 mmol) was dissolved in a 1:1 mixture of THF and methanol (100 mL total), to which was added a saturated $K_2CO_3$ solution in MeOH (15 mL). The mixture stirred for 1 hour, was quenched with a saturated aqueous $NH_4Cl$ solution (50 mL) and then extracted with dichloromethane. The organic fractions were combined and dried over $MgSO_4$, filtered, and finally concentrated in vacuo to give compound 7 as a light brown solid (18.4 g, 68 mmol, 95% yield). $^1$H NMR (500 MHz, Chloroform-d) δ/ppm=7.20 (s, 1H), 7.15 (d, J=1.8 Hz, 1H), 6.96 (d, J=1.8 Hz, 1H), 3.67 (d-broad, J=98.9 Hz, 2H), 3.15 (s, 1H), 1.36 (d-broad, J=168.9 Hz, 12H). $^{13}$C NMR (126 MHz, Chloroform-d) δ/ppm=168.70, 140.86, 140.65, 125.50, 124.16, 122.48, 116.81, 81.97, 78.85, 20.67. HRMS (APCI) calculated for $C_{15}H_{18}N_4O$+H: 271.1553 $[M+H]^+$; found: 271.1557.

Tetradiisopropylbenzamide-triazolophane (OPTz)

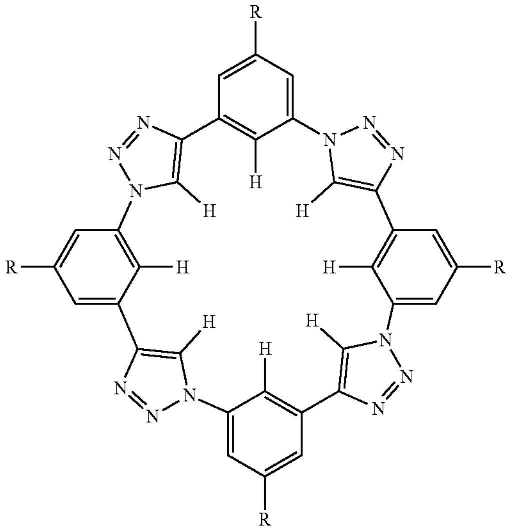

(OPTz)

-continued

R = 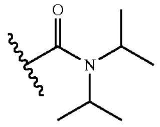

Compound 7 (1.2 g, 4.4 mmol) and tetrabutylammonium chloride (1.2 g, 1.1 mmol) were dissolved in a 2:1:1 mixture of tetrahydrofuran:ethanol:water (160 mL total) and degassed with argon. A degassed solution (2:1:1 tetrahydrofuran:ethanol:water, 16 mL) of copper sulfate pentahydrate (110 mg, 0.44 mmol), TBTA (230 mg, 0.44 mmol), and sodium ascorbate (175 mg, 0.88 mmol) was then added to the solution of compound 7 and stirred under argon for 6 hours at 50° C. The reaction was then cooled to room temperature and the organic solvents (tetrahydrofuran, ethanol) were removed in vacuo. The slurry was then extracted with dichloromethane. The organic phase was then washed with a 1 M solution of ammonium chloride, dried over $MgSO_4$, filtered, and then concentrated in vacuo. The crude product was purified by column chromatography on silica with a 20:1:0.1 mixture of dichloromethane:methanol:triethylamine to give the pure OPTz•TBACl complex as a white solid (4.2 g, 3.1 mmol, 70% yield). The TBACl was then removed by dissolving the complex in dichloromethane followed by washing with deionized water. The organic fractions were then dried over $MgSO_4$, and concentrated in vacuo to give the free macrocycle as a white powder. $^1H$ NMR (500 MHz, DMSO-$d_6$) δ/ppm=10.75 (s, 1H), 8.87 (s, 1H), 7.60-7.57 (m, 2H), 1.45 (s-broad, 12H), and one peak of the isopropyl group overlaps with the residual solvent peak. $^{13}C$ NMR (125 MHz, DMSO-$d_6$) δ/ppm=168.32, 145.67, 140.19, 136.25, 131.78, 126.65, 121.80, 113.49, 59.26, 23.07, 20.57, 19.21, 13.97, 13.49. HRMS (ESI) calculated for $C_{60}H_{72}N_{16}O_4$+Cl: 1115.5616 $[M+Cl]^-$; found: 1115.5584.

Example 4. Investigation of Template Effect on Macrocyclization

To probe the impact of templation on the synthesis of the OPTZ macrocycle, we first tested the necessity of a templating agent by conducting the macrocyclization reaction in the absence of any additional anionic template. Consistent with our expectations based upon the results of our conformational analysis, triazolophane OPTZ was isolated in poor yields (<5%, Table 1) when $Cl^-$ was omitted from the reaction mixture, thus indicating that a template was vital for obtaining the macrocycle in high yields. We next sought to investigate the efficiency of the $Cl^-$ template, namely whether it is deactivated by reversible complexation upon the formation of the OPTZ macrocycle. To test this, we again subjected building block 8 to the CuAAC conditions, except this time with the addition of a substoichiometric amount of $Cl^-$ (0.25 equiv. relative to the macrocyclic product). The addition of a catalytic amount of $Cl^-$ resulted in a 25% yield of the OPTZ macrocycle. This intermediate yield suggests that the chloride template is deactivated by binding to the OPTZ macrocycle as it is produced over the course of the reaction. Furthermore, this is consistent with the characteristically strong binding affinity of triazolophane macrocycles for the $Cl^-$ anion.

Finally, we investigated whether or not this templating effect was generalizable to other anionic guests (Table 1). We hypothesized that as long as the pre-macrocyclic oligomer displayed an affinity for the templating anion, then the number of conformations sampled by the oligomer would be minimized, resulting in the reaction funneling towards the macrocyclic product. To this end, we screened anions that were larger ($BPh_4^-$, $I^-$) and smaller ($F^-$) than chloride. The appropriate tetrabutylamonium salts (1 equiv. relative to the macrocyclic product) were added to the one-pot CuAAC reaction of amide 8 and the yields were determined by $^1H$ NMR analysis (see supporting information). Utilizing $BPh_4^-$ as the templating anion showed no noticeable improvement in yield relative to the template free reaction (<5%). When $I^-$ was used as the templating anion, macrocycle OPTz was obtained in 45% yield. Likewise, macrocycle OPTz was obtained in 40% yield in the presence of templating $F^-$.

TABLE 1

Impact of anionic templates on the yield of OPTZ macrocycles.

| Anion Template | Equivalents of Template Relative to Product | Macrocycle Yield |
|---|---|---|
| $Cl^-$ | 0 | <5% |
| $Cl^-$ | 0.25 | 25% |
| $Cl^-$ | 1.0 | 70% |
| $F^-$ | 1.0 | 40% |
| $I^-$ | 1.0 | 45% |
| $BPh_4^-$ | 1.0 | <5% |

We attribute the variability in macrocycle yield obtained in the presence of different templating anions to how well they match the size of the cavity of the pre-macrocyclic oligomer ($r_{cavity}$≈1.9 Å). The absence of a template effect when the macrocyclization is run in the presence of $BPh_4^-$ likely arises from the poor size match between the anion and receptor ($r_{BPh_4}$≈5.3 Å). In fact, modelling suggests that even if the $BPh_4^-$ anion does bind to the pre-macrocyclic oligomer, the terminal azide and alkyne moieties are spaced too far apart to undergo the final ring closing reaction (see supporting information). Conversely, the good yields in the presence of $I^-$ and $F^-$ are attributed to more appropriate size matches between the oligomeric cavity and anionic templates ($I^-$, $r_{ion}$=2.2 Å; $F^-$, $r_{ion}$=1.3 Å). Our observations suggest that a range of additional anions could serve as templates for the one-pot synthesis of triazolophane macrocycles so long as they don't spatially isolate the terminal azido and alkynyl groups, inhibiting the final ring closing reaction.

Figure 2:
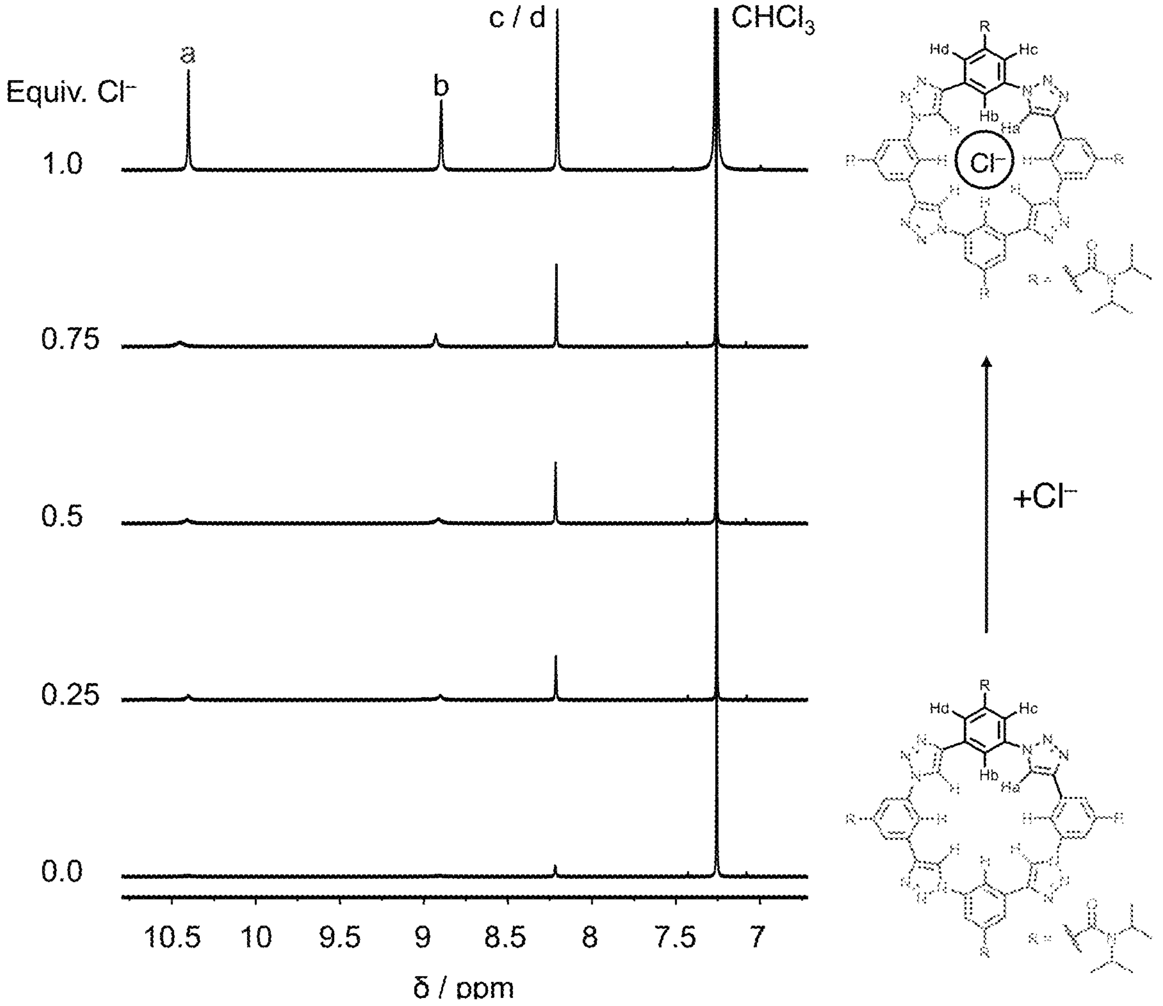
FIG. 2 depicts an exemplary $^1H$ NMR spectra (1 mM, 600 MHz, $CD_2Cl_2$, 298 K) of the aromatic region of the OPTZ macrocycle (triazolophane macrocycle of Formula (IA)) upon the addition of TBACl.

The $^1H$ NMR spectra generated by titration of a halide salt into a solution of the OPTZ macrocycle (FIG. 2) are consistent with the corresponding UV-Vis titrations. $^1H$ NMR titrations were conducted at a concentration of 1 mM in $CD_2Cl_2$ with the titration of $Cl^-$ being representative of the features observed with all of the other anions investigated. In the absence of a guest the aromatic protons of the OPTZ macrocycle are broadened into the baseline, consistent with aggregation of the macrocycle (see supporting information). Upon substoichiometric addition of $Cl^-$, three aromatic peaks of the macrocycle are observed to sharpen and grow from the baseline which then plateaus beyond 1 equiv. of $Cl^-$. Interestingly, this plateau at 1 equiv. of $Cl^-$ was not observed with previous triazolophane species, suggesting that the higher symmetry of the OPTZ macrocycle may promote these high fidelity anion-receptor complexes.

Figure 3A:
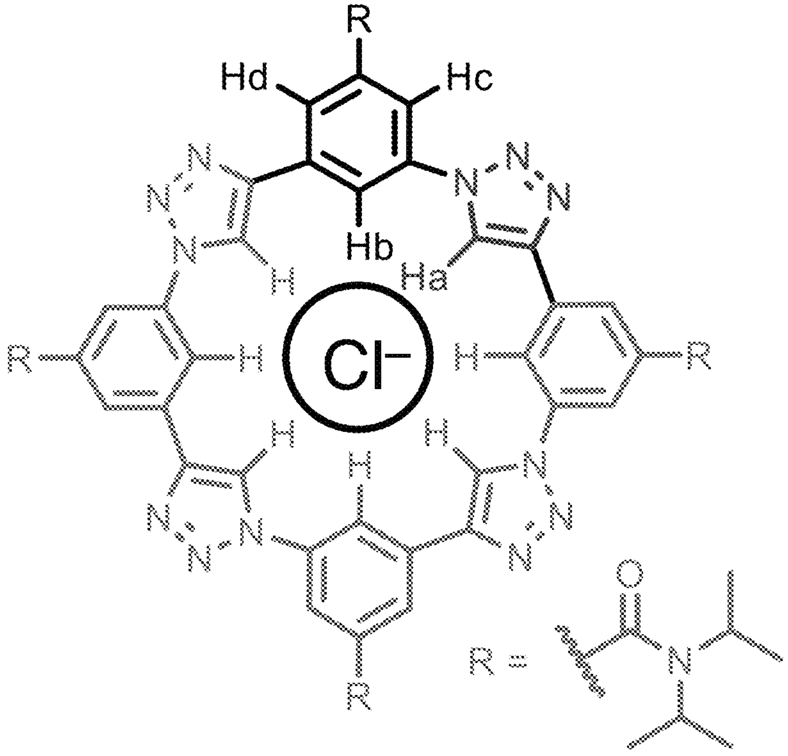
FIG. 3A depicts a complex of chloride with the OPTZ macrocycle (triazolophane macrocycle of Formula (I)).
Figure 3B:
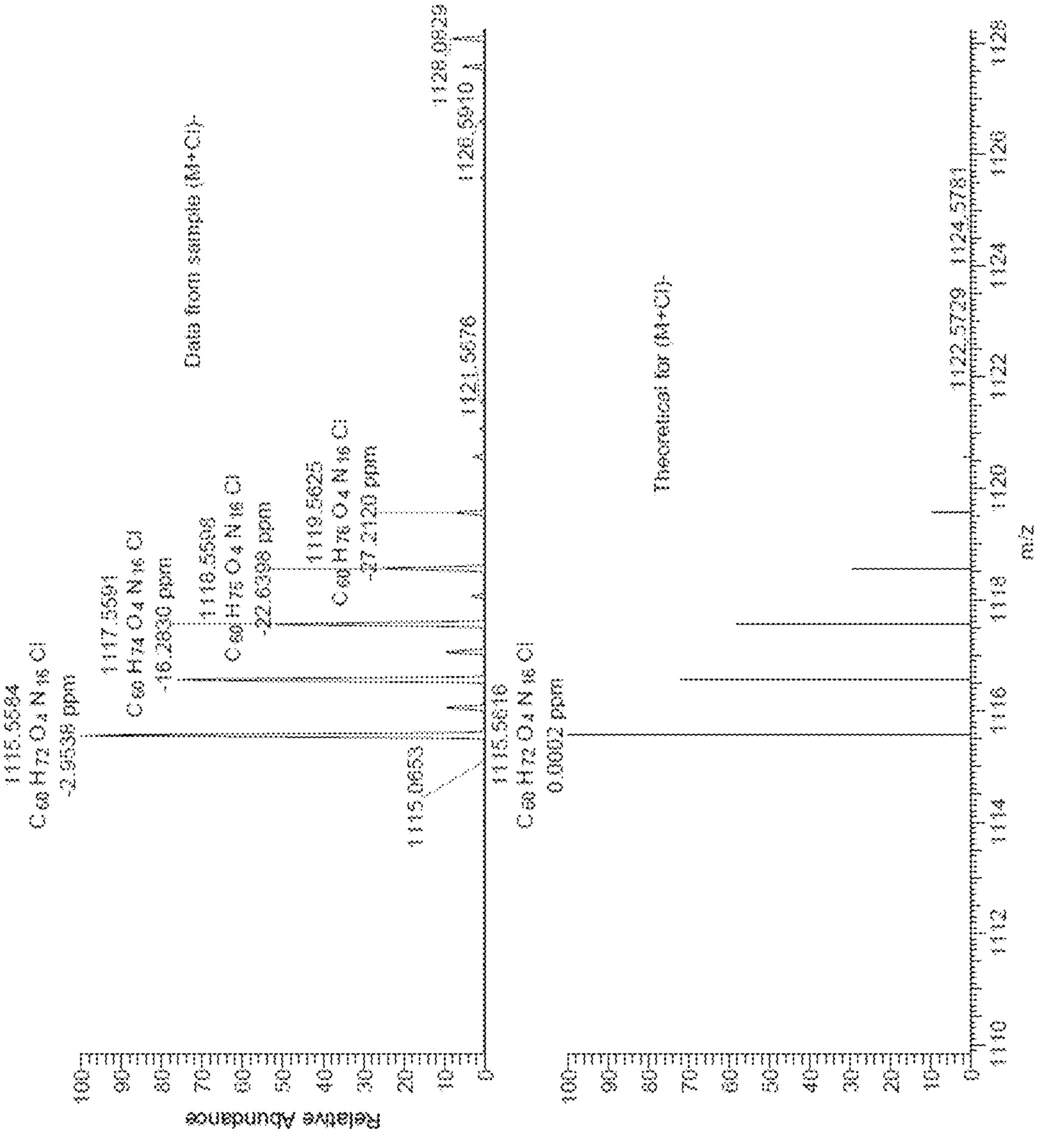
FIG. 3B depicts an exemplary high resolution electrospray mass spectrum of the OPTZ macrocycle (triazolophane macrocycle of Formula (I)) upon the addition of TBACl.

The high resolution mass spectrum generated by titration of a chloride salt into a solution of the OPTZ macrocycle (FIG. 3) is consistent with the formation of a 1:1 complex between the OPTZ macrocycle and the chloride anion.

INCORPORATION BY REFERENCE

U.S. Pat. Nos. 9,701,621, 10,077,233 and 10,202,395 are directed to compositions, methods and complexes of analogous technologies disclosed herein. All literature, publications, patents, patent applications, appendices, and related material cited here are incorporated by reference as if fully set forth herein.

What is claimed is:

1. A triazolophane macrocycle of Formula (I) comprising:

(I)

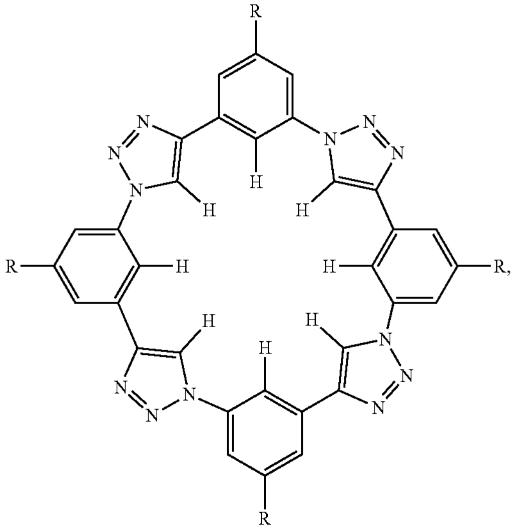

wherein the substituents R are independently selected from the group consisting of a linear and branched alkyl, a linear and branched alkyl substituted with an ionizable functional group such as an amine or carboxylic acid, a linear and branched alkoxy —$OR^3$, where $R^3$ is any alkyl, an alkyl comprising —$O(CH_2CH_2O)_nCH_3$, where n is 1-20, an amide —CO—$NR^1R^2$, where $R^1$ is any alkyl, $R^2$ is any alkyl, wherein $R^1$ and $R^2$ may be identical or different, —OCO—$R^4$, wherein $R^4$ is any alkyl, an aromatic ring or their substituted analogues, any length and sequence of natural and unnatural amino acids that make up a peptide chain, and —C≡C—$R^5$ where $R^5$ is any alkyl.

2. The triazolophane macrocycle of Formula (I) according to claim 1, wherein the substituents R are identical.

3. The triazolophane macrocycle of Formula (I) according to claim 1, wherein the triazolophane macrocycle of Formula (I) consists of Formula (IA):

(IA)

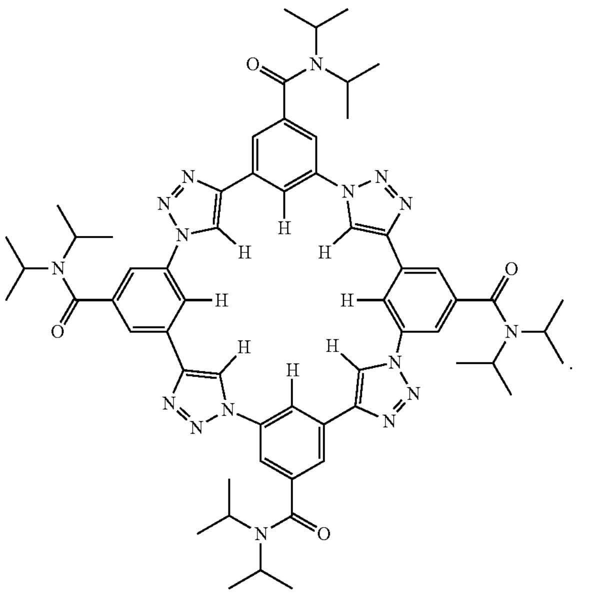

4. A method of synthesizing a triazolophane macrocycle of Formula (I) according to claim 1, the method comprising: converting

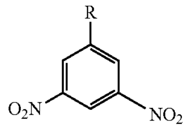

in a single-pot synthesis according to Scheme (I):

(Scheme (I)).

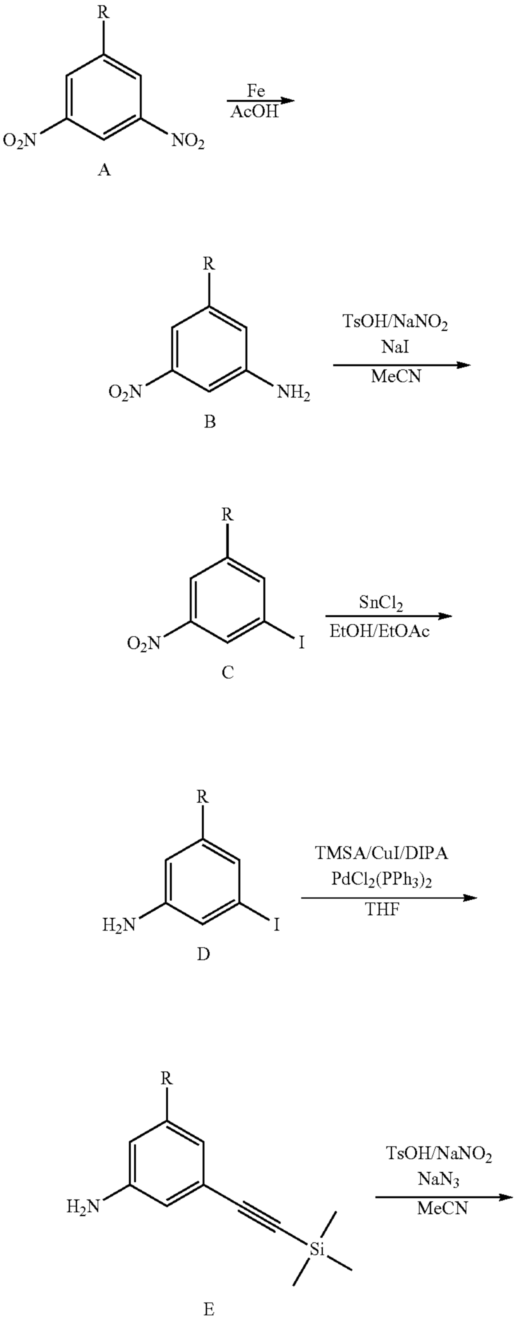

-continued

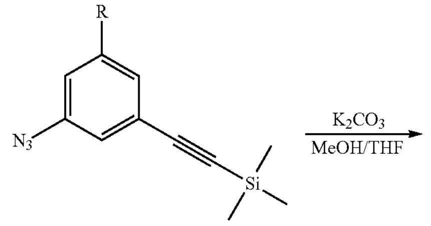

F

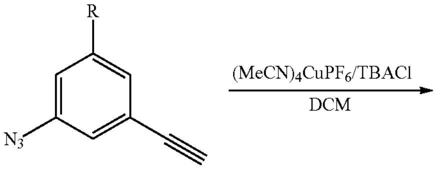

G

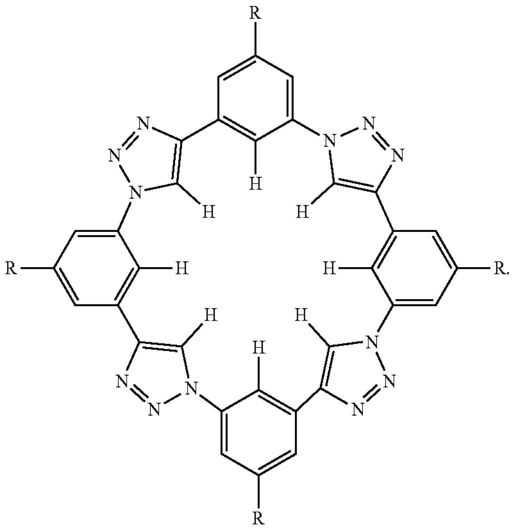

(I)

5. The method of synthesizing the triazolophane macrocycle of Formula (I) according to claim 4, wherein the substituents R are identical.

6. The method of synthesizing the triazolophane macrocycle of Formula (I) according to claim 4, wherein the triazolophane macrocycle of Formula (I) consists of Formula (IA):

(IA)

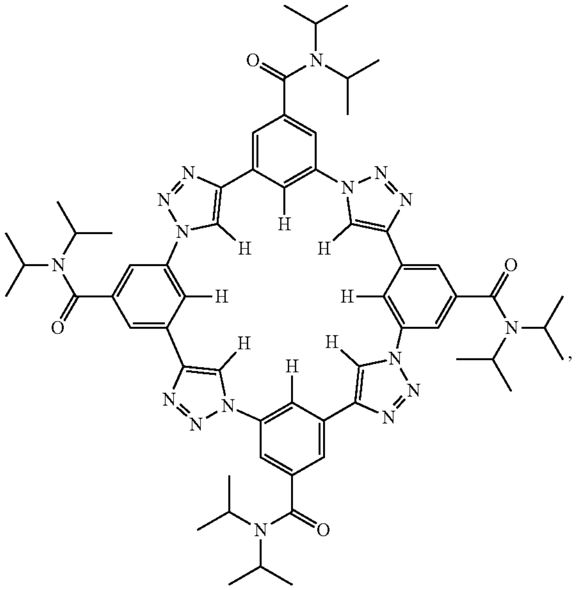

wherein the method comprises converting

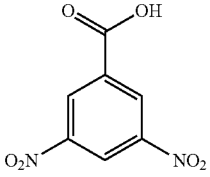 [SMILES: O=C(O)c1cc([N+](=O)[O-])cc([N+](=O)[O-])c1]

in a single-pot synthesis according to Scheme (IA):

(Schene (IA)).

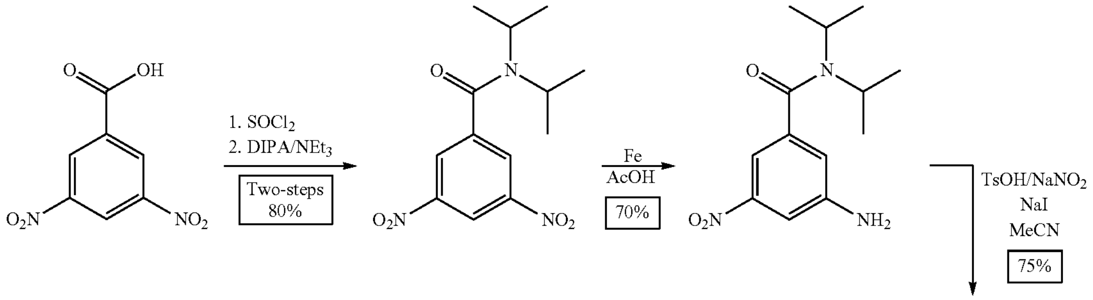

-continued
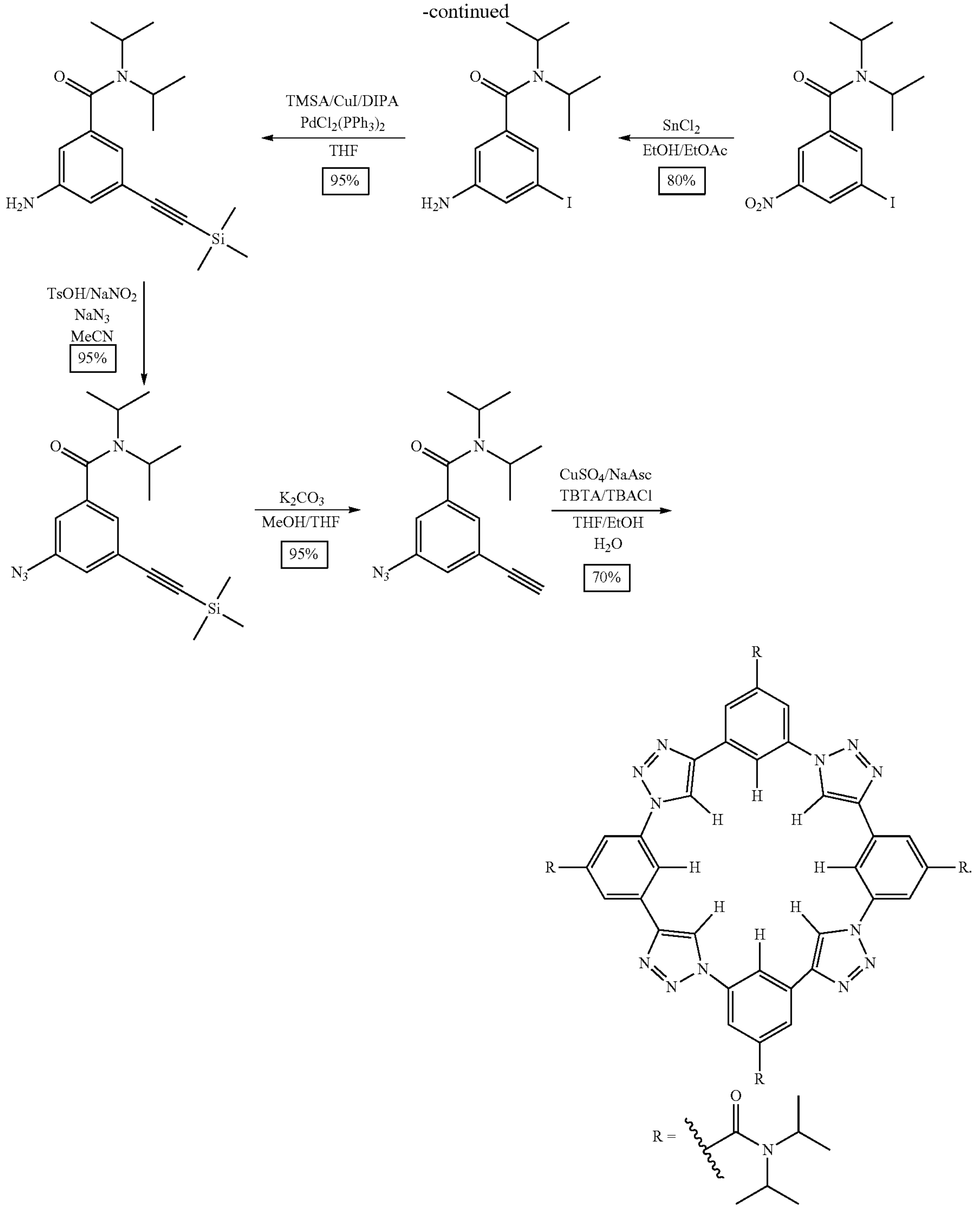
7. A method of increasing the yield and scale of the single-pot synthesis of triazolophane macrocycle of Formula (I) according to claim 1, the method comprising reacting
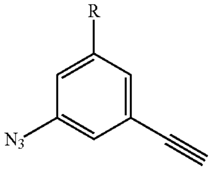

in the presence of a halide salt as a template according to Scheme (X):

(Scheme (X))

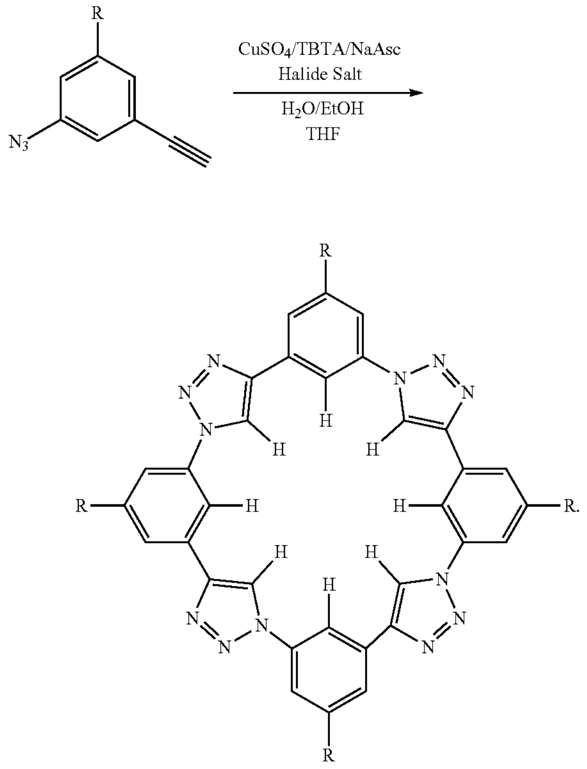

8. The method of increasing the yield and scale of the single-pot synthesis of the triazolophane macrocycle of Formula (I) according to claim 7, wherein the substituents R are identical.

9. The method of increasing the yield and scale of the single-pot synthesis of the triazolophane macrocycle of Formula (I) according to claim 7, the method comprising reacting

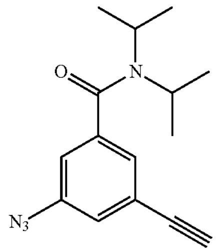 [SMILES: C#Cc1cc(N=[N+]=[N-])cc(C(=O)N(C(C)C)C(C)C)c1]

in the presence of the halide salt as a template according to Scheme (Y):

(Scheme (Y).

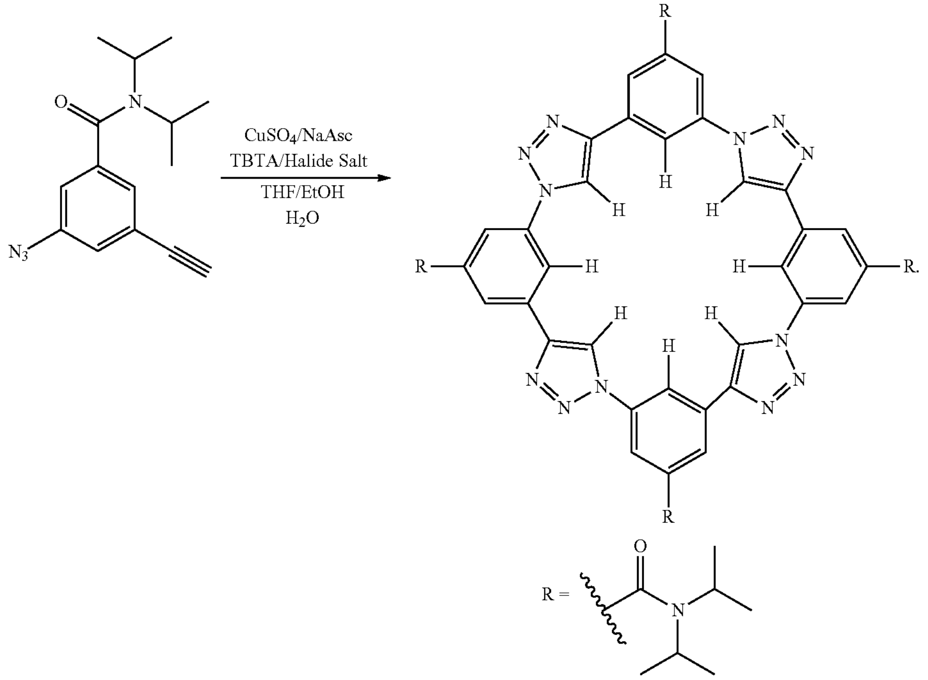

10. The method of claim 7, wherein the halide salt comprises an anion selected from the group consisting of chloride, fluoride and iodide.

11. The method of claim 7, wherein the halide salt is a chloride salt.

12. The method of claim 11, wherein the chloride salt is tetrabutylammonium chloride.

13. A complex comprising:

(a) an anion; and (b) a triazolophane macrocycle of Formula (I) according to claim 1.

14. The complex according to claim 13, wherein the triazolophane macrocycle of Formula (I) has identical substituents R.

15. The complex according to claim 13, wherein the triazolophane macrocycle of Formula (I) consists of Formula (IA):

(IA)

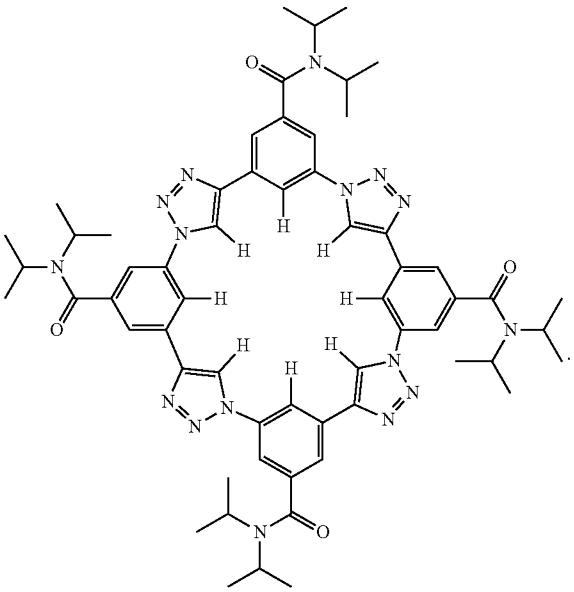

16. The complex of claim 13, wherein the anion is selected from the group consisting of chloride, fluoride, iodide, bromide, hydroxide, sulfide, hydrogen sulfide, cyanide, azide, organosulfides, alkoxides, bifluoride, borohydride, tetrafluoroborate, hydride, bisulfide, selenide, hydrogen selenide, superoxide, peroxide, and hypochlorite.

17. The complex of claim 13, wherein a ratio of the complex comprising the triazolophane macrocycle of Formula (I):anion is selected from the group consisting of 1:1 (macrocycle:anion), 2:1 (macrocycle:anion), and 3:2 (macrocycle:anion).

18. A method of removing an anion from a solution containing the anion, wherein the method comprises:

(a) contacting the solution with a triazolophane macrocycle of Formula (I) according to claim 1;

(b) forming a complex, said complex comprising the anion and the triazolophane macrocycle of Formula (I); and (c) removing the complex from the solution.

19. The method of removing an anion from a solution containing the anion according to claim 18, wherein the triazolophane macrocycle of Formula (I) has identical substituents R.

20. The method of removing an anion from a solution containing the anion according to claim 18, wherein the triazolophane macrocycle of Formula (I) consists of Formula (IA):

(IA)

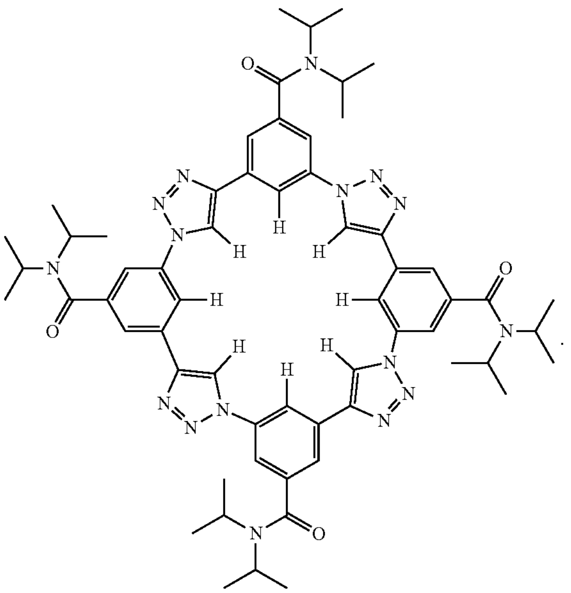

* * * * *